US012744115B2

(12) United States Patent
Raciti et al.

(10) Patent No.: US 12,744,115 B2
(45) Date of Patent: Sep. 22, 2026

(54) SYSTEMS AND METHODS FOR PROCESSING ELECTRONIC IMAGES WITH METADATA INTEGRATION

(71) Applicant: PAIGE.AI, Inc., New York, NY (US)

(72) Inventors: Patricia Raciti, New York, NY (US); Jeremy Daniel Kunz, New York, NY (US); Christopher Kanan, Pittsford, NY (US); Zahra Ebrahimzadeh, New York, NY (US)

(73) Assignee: Paige.AI, Inc., New York, NY (US)

( * ) Notice: Subject to any disclaimer, the term of this patent is extended or adjusted under 35 U.S.C. 154(b) by 918 days.

(21) Appl. No.: 17/877,585

(22) Filed: Jul. 29, 2022

(65) Prior Publication Data

US 2023/0061428 A1 Mar. 2, 2023

Related U.S. Application Data

(60) Provisional application No. 63/260,369, filed on Aug. 18, 2021.

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0012* (2013.01); *G16H 30/20* (2018.01); *G16H 50/20* (2018.01); *G06T 2207/30096* (2013.01)

(58) Field of Classification Search
CPC ........ G16H 30/40; G16H 30/20; G16H 50/20; G06T 7/0012
See application file for complete search history.

(56) References Cited

U.S. PATENT DOCUMENTS 9,547,898 B2 * 1/2017 Häll ...................... G06T 7/0012
10,825,552 B2 11/2020 Sanborn et al.
(Continued)

FOREIGN PATENT DOCUMENTS

WO 2020204635 A1 10/2020

OTHER PUBLICATIONS

Costa, Daniel N. et al: "MR Imaging?Transrectal US Fusion for Targeted Prostate Biopsies: Implications for Diagnosis and Clinical Management", Radiographics., vol. 35, No. 3, May 1, 2015 (May 1, 2015), pp. 696-708, XP055825267, US ISSN: 0271-5333, DOI: 10.1148/rg.2015140058.

(Continued)

*Primary Examiner* — Mohammed H Zuberi
(74) *Attorney, Agent, or Firm* — Bookoff McAndrews, PLLC

(57) ABSTRACT

A computer-implemented method for processing medical images, the method may include receiving a plurality of medical images of at least one pathology specimen, the pathology specimen being associated with a patient. The method may further include receiving a gross description, the gross description comprising data about the medical images. The method may next include extracting data from the description. Next, the method may include determining, using a machine learning system, at least one associated location on the medical images for one or more pieces of data extracted. The method may then include outputting a visual indication of the gross description data displayed in relation to the medical images.

20 Claims, 22 Drawing Sheets

(51) Int. Cl.

| | |
|---|---|
| ***G16H 30/20*** | (2018.01) |
| ***G16H 50/20*** | (2018.01) |

(56) References Cited

U.S. PATENT DOCUMENTS

| | | | | |
|---|---|---|---|---|
| 11,354,838 | B2 * | 6/2022 | Matsuzawa | A01C 21/007 |
| 11,675,178 | B2 * | 6/2023 | Wirch | G02B 21/34<br>382/226 |
| 11,681,418 | B2 * | 6/2023 | Wirch | G06F 18/217<br>382/128 |
| 12,198,811 | B2 * | 1/2025 | Tsuyama | G02B 21/34 |
| 2009/0234671 | A1 * | 9/2009 | Jones | G06Q 30/04<br>705/2 |
| 2015/0279026 | A1 * | 10/2015 | Häll | G06V 20/69<br>382/128 |
| 2016/0364862 | A1 * | 12/2016 | Reicher | G06F 3/0482 |
| 2018/0046759 | A1 * | 2/2018 | Barral | G06V 20/698 |
| 2020/0381104 | A1 * | 12/2020 | Ceballos Lentini | G16H 30/40 |
| 2021/0233642 | A1 * | 7/2021 | Sue | G16H 30/40 |
| 2021/0350166 | A1 * | 11/2021 | Sue | G16H 30/40 |
| 2021/0398278 | A1 * | 12/2021 | Locke | G06T 7/0012 |
| 2022/0301670 | A1 * | 9/2022 | Sharma | G06F 40/279 |
| 2023/0131675 | A1 * | 4/2023 | Kunz | G16H 10/20<br>382/128 |

OTHER PUBLICATIONS

Park, Hyun-Joo et al: "Semi-automated method for estimating lesion volumes", Journal of Neuroscience Methods, Elsevier Science Publisher B. V., Amsterdam, NL, vol. 213, No. 1, Dec. 20, 2012 (Dec. 20, 2012), pp. 76-83, XP028973398, ISSN:.0165-0270, DOI: 10.1016/J.JNEUMETH.2012.12.010.

Hunter, Tammy, and Ernest Ward. "Skin Biopsy in Dogs: VCA Animal Hospital." VCA Animal Hospital, https://vcahospitals.com/know-your-pet/skin-biopsy-in-dogs.

Stoewen, Debbie, and Joan Rest. "Cytology-Histopathology-Biopsies: VCA Animal Hospital." VCA Animal Hospital, https://vcahospitals.com/know-your-pet/cytology-histopathology-biopsies.

* cited by examiner

Figure 2:
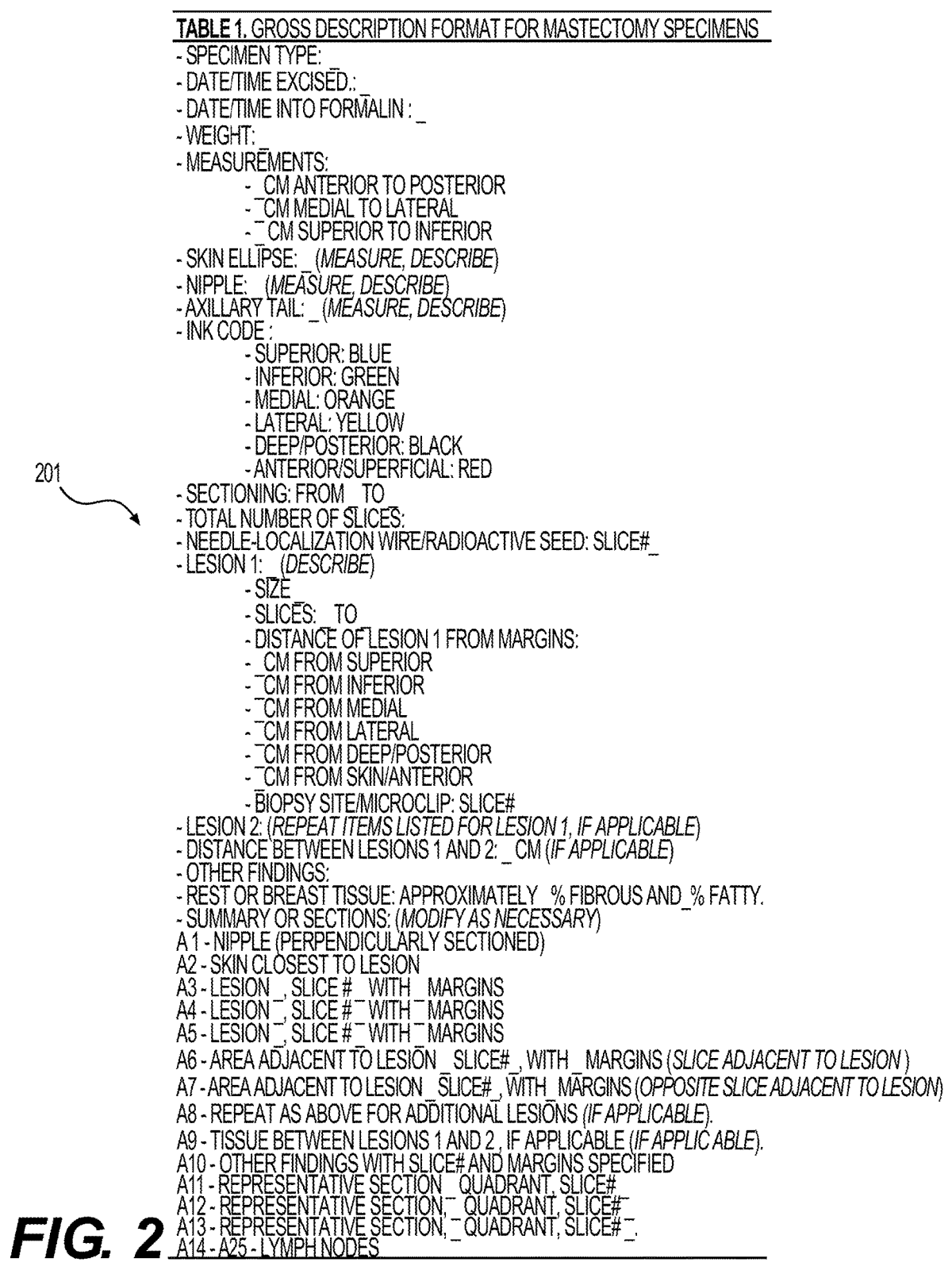

TABLE 1. GROSS DESCRIPTION FORMAT FOR MASTECTOMY SPECIMENS

- SPECIMEN TYPE: _
- DATE/TIME EXCISED.: _
- DATE/TIME INTO FORMALIN : _
- WEIGHT: _
- MEASUREMENTS:
    - _ CM ANTERIOR TO POSTERIOR
    - _ CM MEDIAL TO LATERAL
    - _ CM SUPERIOR TO INFERIOR
- SKIN ELLIPSE: _ (*MEASURE, DESCRIBE*)
- NIPPLE: _ (*MEASURE, DESCRIBE*)
- AXILLARY TAIL: _ (*MEASURE, DESCRIBE*)
- INK CODE :
    - SUPERIOR: BLUE
    - INFERIOR: GREEN
    - MEDIAL: ORANGE
    - LATERAL: YELLOW
    - DEEP/POSTERIOR: BLACK
    - ANTERIOR/SUPERFICIAL: RED
- SECTIONING: FROM _ TO
- TOTAL NUMBER OF SLICES:
- NEEDLE-LOCALIZATION WIRE/RADIOACTIVE SEED: SLICE# _
- LESION 1: _ (*DESCRIBE*)
    - SIZE
    - SLICES: _ TO
    - DISTANCE OF LESION 1 FROM MARGINS:
    - _ CM FROM SUPERIOR
    - _ CM FROM INFERIOR
    - _ CM FROM MEDIAL
    - _ CM FROM LATERAL
    - _ CM FROM DEEP/POSTERIOR
    - _ CM FROM SKIN/ANTERIOR
    - BIOPSY SITE/MICROCLIP: SLICE#
- LESION 2: (*REPEAT ITEMS LISTED FOR LESION 1, IF APPLICABLE*)
- DISTANCE BETWEEN LESIONS 1 AND 2: _ CM (*IF APPLICABLE*)
- OTHER FINDINGS:
- REST OR BREAST TISSUE: APPROXIMATELY _% FIBROUS AND _% FATTY.
- SUMMARY OR SECTIONS: (*MODIFY AS NECESSARY*)

A 1 - NIPPLE (PERPENDICULARLY SECTIONED)
A2 - SKIN CLOSEST TO LESION
A3 - LESION _, SLICE # _ WITH _ MARGINS
A4 - LESION _, SLICE # _ WITH _ MARGINS
A5 - LESION _, SLICE # _ WITH _ MARGINS
A6 - AREA ADJACENT TO LESION _ SLICE# _, WITH _ MARGINS (*SLICE ADJACENT TO LESION*)
A7 - AREA ADJACENT TO LESION _ SLICE# _, WITH _ MARGINS (*OPPOSITE SLICE ADJACENT TO LESION*)
A8 - REPEAT AS ABOVE FOR ADDITIONAL LESIONS (*IF APPLICABLE*).
A9 - TISSUE BETWEEN LESIONS 1 AND 2 , IF APPLICABLE (*IF APPLIC ABLE*).
A10 - OTHER FINDINGS WITH SLICE# AND MARGINS SPECIFIED
A11 - REPRESENTATIVE SECTION _ QUADRANT, SLICE# _
A12 - REPRESENTATIVE SECTION, _ QUADRANT, SLICE# _.
A13 - REPRESENTATIVE SECTION, _ QUADRANT, SLICE# _.
A14 - A25 - LYMPH NODES

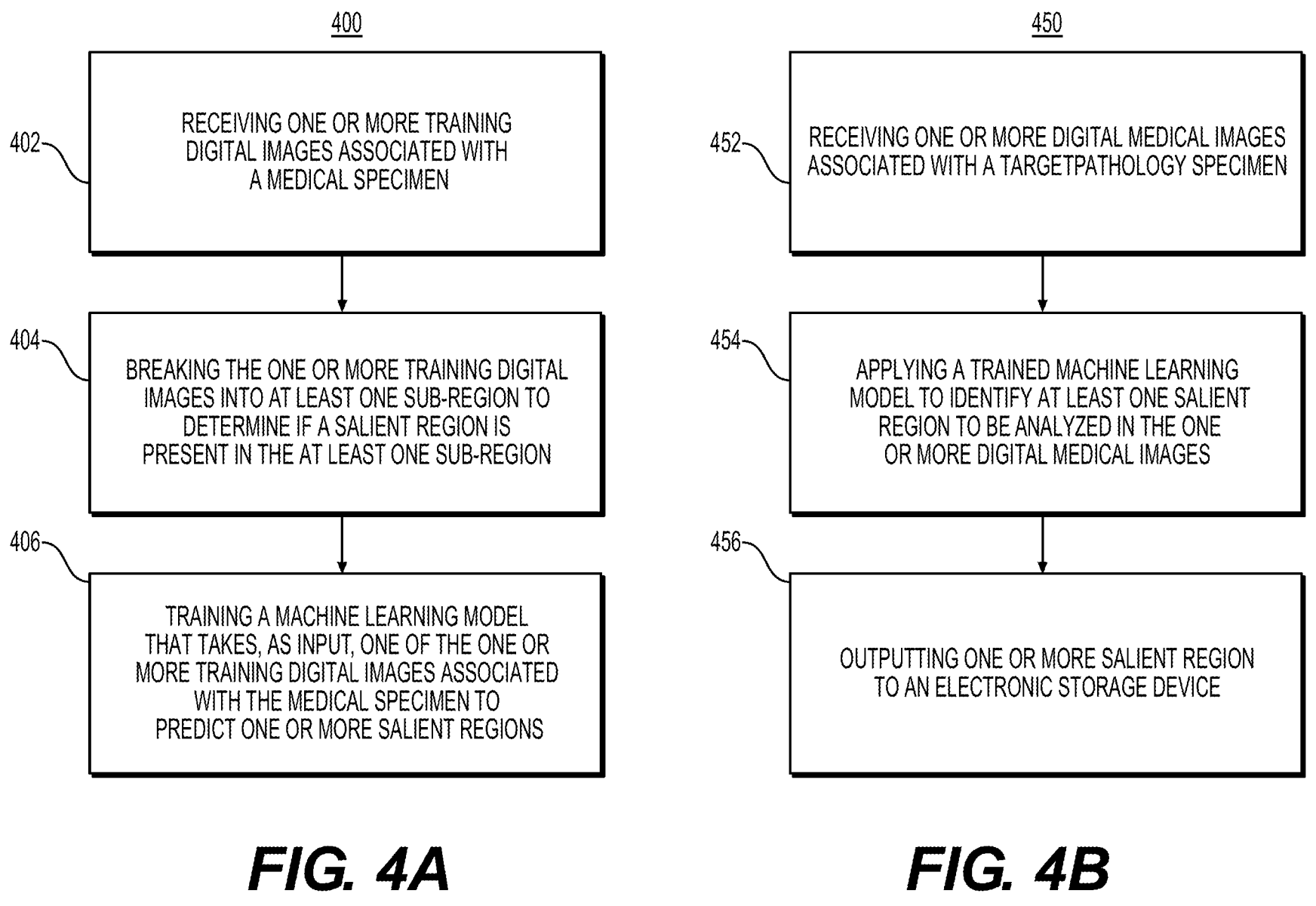

402 RECEIVING ONE OR MORE TRAINING DIGITAL IMAGES ASSOCIATED WITH A MEDICAL SPECIMEN

404 BREAKING THE ONE OR MORE TRAINING DIGITAL IMAGES INTO AT LEAST ONE SUB-REGION TO DETERMINE IF A SALIENT REGION IS PRESENT IN THE AT LEAST ONE SUB-REGION

406 TRAINING A MACHINE LEARNING MODEL THAT TAKES, AS INPUT, ONE OF THE ONE OR MORE TRAINING DIGITAL IMAGES ASSOCIATED WITH THE MEDICAL SPECIMEN TO PREDICT ONE OR MORE SALIENT REGIONS

452 RECEIVING ONE OR MORE DIGITAL MEDICAL IMAGES ASSOCIATED WITH A TARGETPATHOLOGY SPECIMEN

454 APPLYING A TRAINED MACHINE LEARNING MODEL TO IDENTIFY AT LEAST ONE SALIENT REGION TO BE ANALYZED IN THE ONE OR MORE DIGITAL MEDICAL IMAGES

456 OUTPUTTING ONE OR MORE SALIENT REGION TO AN ELECTRONIC STORAGE DEVICE

FIG. 4B

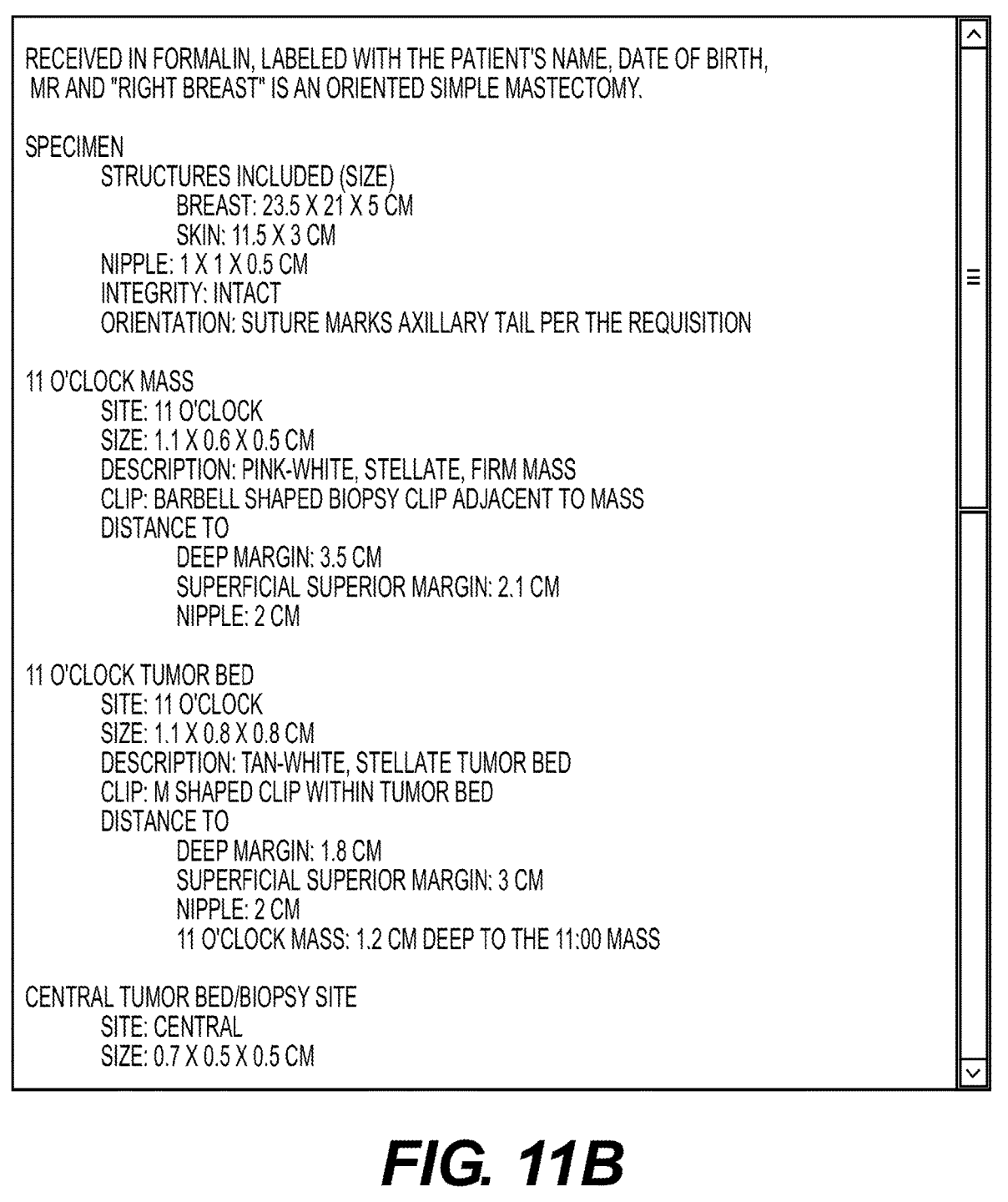

RECEIVED IN FORMALIN, LABELED WITH THE PATIENT'S NAME, DATE OF BIRTH, MR AND "RIGHT BREAST" IS AN ORIENTED SIMPLE MASTECTOMY.

SPECIMEN
STRUCTURES INCLUDED (SIZE)
BREAST: 23.5 X 21 X 5 CM
SKIN: 11.5 X 3 CM
NIPPLE: 1 X 1 X 0.5 CM
INTEGRITY: INTACT
ORIENTATION: SUTURE MARKS AXILLARY TAIL PER THE REQUISITION

11 O'CLOCK MASS
SITE: 11 O'CLOCK
SIZE: 1.1 X 0.6 X 0.5 CM
DESCRIPTION: PINK-WHITE, STELLATE, FIRM MASS
CLIP: BARBELL SHAPED BIOPSY CLIP ADJACENT TO MASS
DISTANCE TO
DEEP MARGIN: 3.5 CM
SUPERFICIAL SUPERIOR MARGIN: 2.1 CM
NIPPLE: 2 CM

11 O'CLOCK TUMOR BED
SITE: 11 O'CLOCK
SIZE: 1.1 X 0.8 X 0.8 CM
DESCRIPTION: TAN-WHITE, STELLATE TUMOR BED
CLIP: M SHAPED CLIP WITHIN TUMOR BED
DISTANCE TO
DEEP MARGIN: 1.8 CM
SUPERFICIAL SUPERIOR MARGIN: 3 CM
NIPPLE: 2 CM
11 O'CLOCK MASS: 1.2 CM DEEP TO THE 11:00 MASS

CENTRAL TUMOR BED/BIOPSY SITE
SITE: CENTRAL
SIZE: 0.7 X 0.5 X 0.5 CM

FIG. 11B

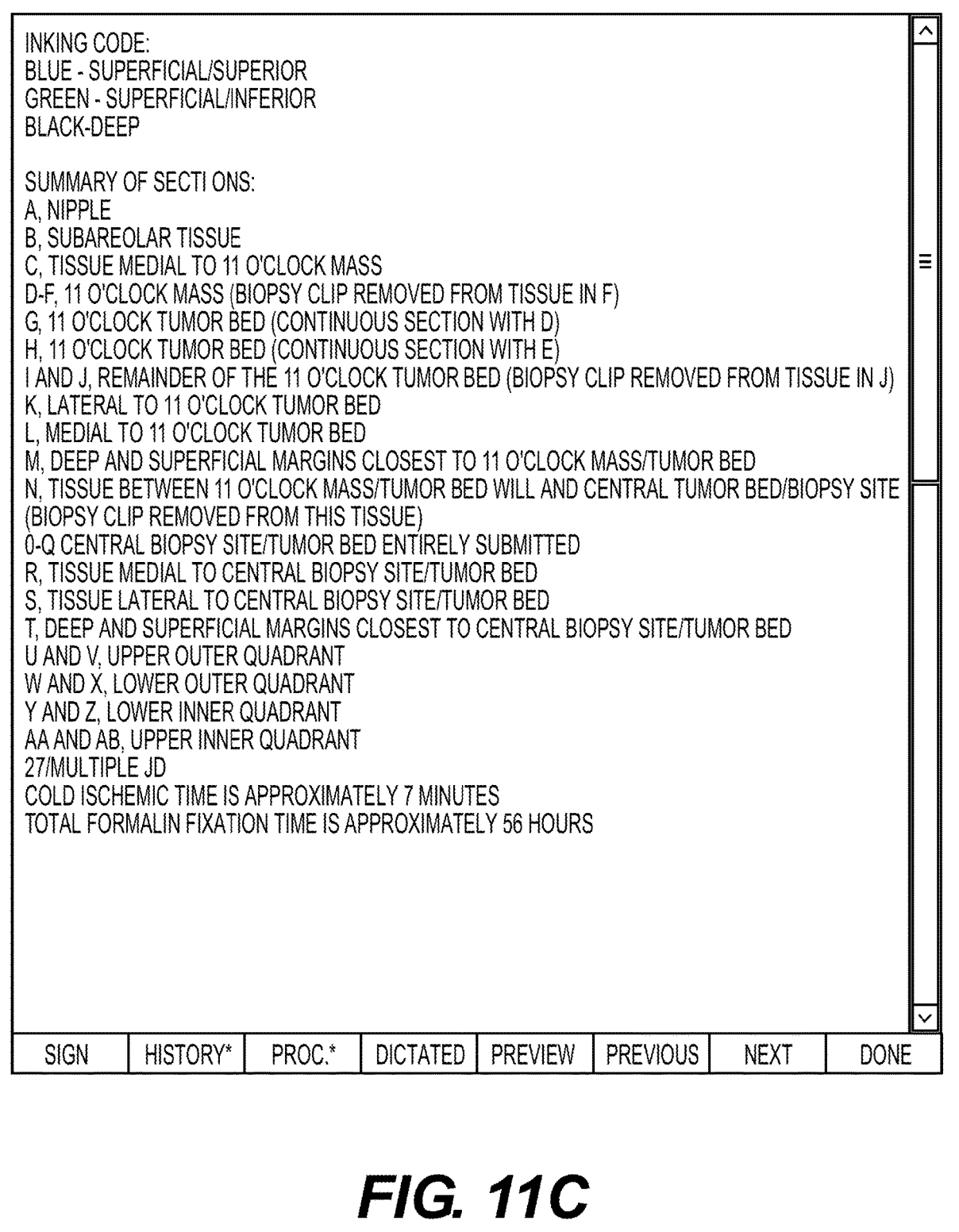

INKING CODE:
BLUE - SUPERFICIAL/SUPERIOR
GREEN - SUPERFICIAL/INFERIOR
BLACK-DEEP

SUMMARY OF SECTI ONS:
A, NIPPLE
B, SUBAREOLAR TISSUE
C, TISSUE MEDIAL TO 11 O'CLOCK MASS
D-F, 11 O'CLOCK MASS (BIOPSY CLIP REMOVED FROM TISSUE IN F)
G, 11 O'CLOCK TUMOR BED (CONTINUOUS SECTION WITH D)
H, 11 O'CLOCK TUMOR BED (CONTINUOUS SECTION WITH E)
I AND J, REMAINDER OF THE 11 O'CLOCK TUMOR BED (BIOPSY CLIP REMOVED FROM TISSUE IN J)
K, LATERAL TO 11 O'CLOCK TUMOR BED
L, MEDIAL TO 11 O'CLOCK TUMOR BED
M, DEEP AND SUPERFICIAL MARGINS CLOSEST TO 11 O'CLOCK MASS/TUMOR BED
N, TISSUE BETWEEN 11 O'CLOCK MASS/TUMOR BED WILL AND CENTRAL TUMOR BED/BIOPSY SITE (BIOPSY CLIP REMOVED FROM THIS TISSUE)
0-Q CENTRAL BIOPSY SITE/TUMOR BED ENTIRELY SUBMITTED
R, TISSUE MEDIAL TO CENTRAL BIOPSY SITE/TUMOR BED
S, TISSUE LATERAL TO CENTRAL BIOPSY SITE/TUMOR BED
T, DEEP AND SUPERFICIAL MARGINS CLOSEST TO CENTRAL BIOPSY SITE/TUMOR BED
U AND V, UPPER OUTER QUADRANT
W AND X, LOWER OUTER QUADRANT
Y AND Z, LOWER INNER QUADRANT
AA AND AB, UPPER INNER QUADRANT
27/MULTIPLE JD
COLD ISCHEMIC TIME IS APPROXIMATELY 7 MINUTES
TOTAL FORMALIN FIXATION TIME IS APPROXIMATELY 56 HOURS

| SIGN | HISTORY* | PROC.* | DICTATED | PREVIEW | PREVIOUS | NEXT | DONE |
|---|---|---|---|---|---|---|---|

FIG. 11C

SYSTEMS AND METHODS FOR PROCESSING ELECTRONIC IMAGES WITH METADATA INTEGRATION

RELATED APPLICATION(S)

This application claims priority to U.S. Provisional Application No. 63/260,369 filed Aug. 18, 2021, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods for integrating spatial and orientation information from a gross description of a pathology report for display with a whole slide image (WSI).

BACKGROUND

Accurate pathologic diagnosis and reporting may depend not only on examination of tissue on hematoxylin and eosin (H&E) stained slides but also from contextual knowledge found in a "gross description" of a pathology report (see FIG. 2 showing an example of a gross description). The gross description may include valuable contextual information relating to a whole slide image (WSI) including, but not limited to, a specific lesion sample (especially if multiple are present), a location of the lesion relative to certain clinically relevant landmarks (including surgical margins), and numbers and sectioning patterns of small ancillary organs removed with tumor tissue called lymph nodes.

However, when a physician grosses (i.e., inspects, prepares and sections/slices) lesions from a tissue sample and then observes these grossed lesions under a microscope, the physician might not readily recognize where these lesions were initially located within the sample without referring back to the gross description or some other legend or key. Switching between a gross description and a microscope may be burdensome and time consuming.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic medical images, comprising: receiving a plurality of medical images of at least one pathology specimen, the pathology specimen being associated with a patient; receiving a gross description, the gross description comprising data about the medical images; extracting data from the gross description; determining, using a machine learning system, at least one associated location on the medical images for one or more pieces of data extracted; and outputting a visual indication of the gross description data displayed in relation to the medical images.

A system for processing electronic digital medical images, the system including: at least one memory storing instructions; and at least one processor configured to execute the instructions to perform operations including: receiving a plurality of medical images of at least one pathology specimen, the pathology specimen being associated with a patient; receiving a gross description, the gross description comprising data about the medical images; extracting data from the gross description; determining, using a machine learning system, at least one associated location on the medical images for one or more pieces of data extracted; and outputting a visual indication of the gross description data displayed in relation to the medical images.

A non-transitory computer-readable medium storing instructions that, when executed by a processor, perform operations processing electronic digital medical images, the operations including: receiving a plurality of medical images of at least one pathology specimen, the pathology specimen being associated with a patient; receiving a gross description, the gross description comprising data about the medical images; extracting data from the gross description; determining, using a machine learning system, at least one associated location on the medical images for one or more pieces of data extracted; and outputting a visual indication of the gross description data displayed in relation to the medical images.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2 illustrates an exemplary gross description containing a gross description according to an exemplary embodiment of the present disclosure.

FIG. 4A is a flowchart illustrating how to train an algorithm for image region detection, according to techniques presented herein.

FIG. 4B is a flowchart illustrating methods for image region detection, according to one or more exemplary embodiments herein.

FIG. 11B illustrates a gross description generated for the right breast of FIG. 11A.

FIG. 11C illustrates an example "summary of sections" along with an inking code in the gross description of FIG. 11B.

DESCRIPTION OF THE EMBODIMENTS

Figure 1A:
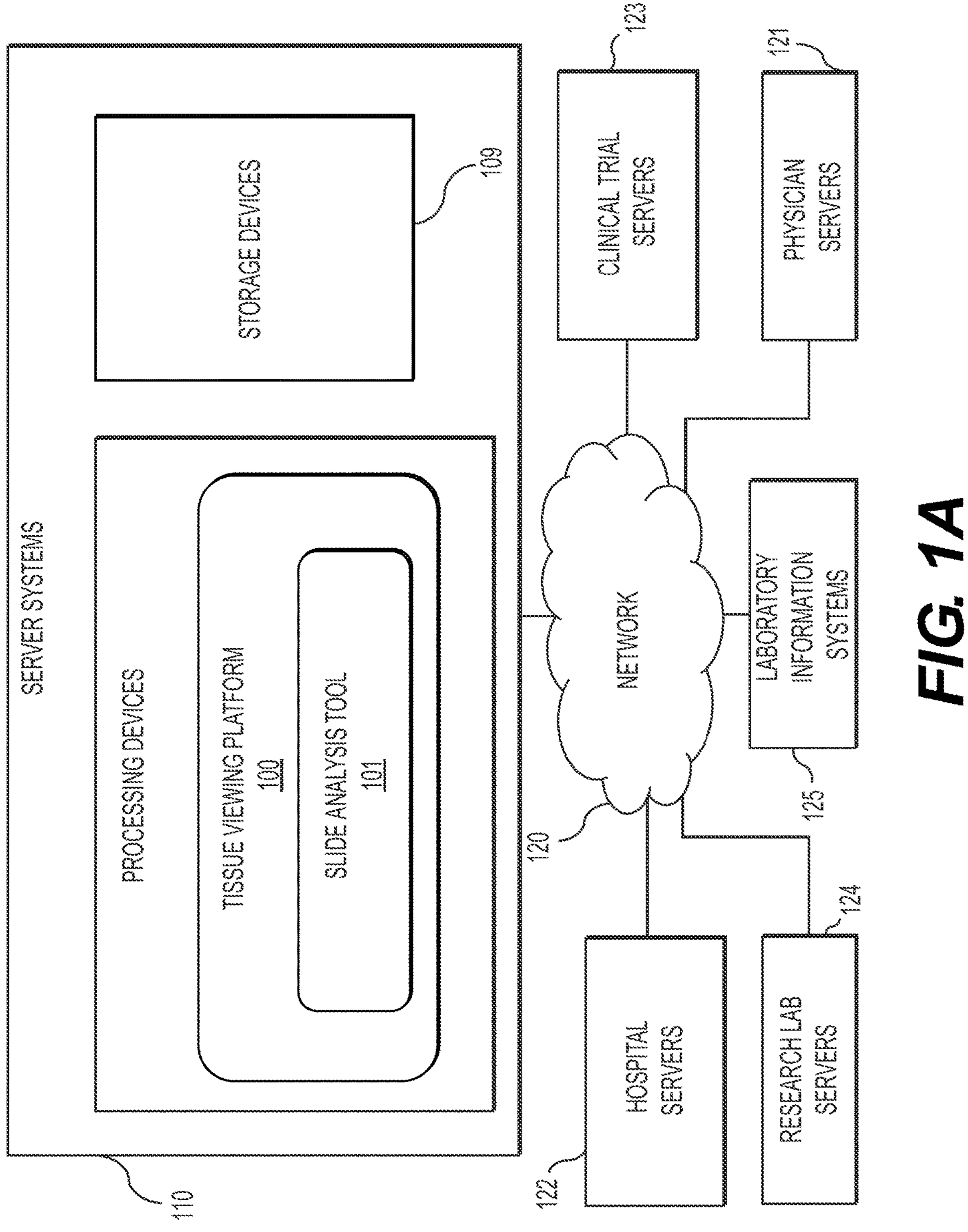
FIG. 1A illustrates an exemplary block diagram of a system and network for processing images, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Techniques presented herein describe extracting information of a patient and integrating spatial and orientation information onto a medic digital image using computer vision and/or machine learning.

Techniques presented herein may relate to using medical images, gross descriptions, and additional information while using image processing techniques and/or machine learning to display additional medical image onto medical digital images.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch, or batch-based, etc.

FIG. 1A illustrates a block diagram of a system and network for processing images, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices that are configured to implement a tissue viewing platform 100, which includes a slide analysis tool 01 for determining specimen property or image property information pertaining to digital pathology image(s), and using machine learning to classify a specimen, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125. However, the correct tissue classification information is not always paired with the image content. Additionally, even if a laboratory information system is used to access the specimen type for a digital pathology image, this label may be incorrect due to the face that many components of a laboratory information system may be manually input, leaving a large margin for error. According to an exemplary embodiment of the present disclosure, a specimen type may be identified without needing to access the laboratory information systems 125, or may be identified to possibly correct laboratory information systems 125. For example, a third party may be given anonymized access to the image content without the corresponding specimen type label stored in the laboratory information system. Additionally, access to laboratory information system content may be limited due to its sensitive content.

Figure 1B:
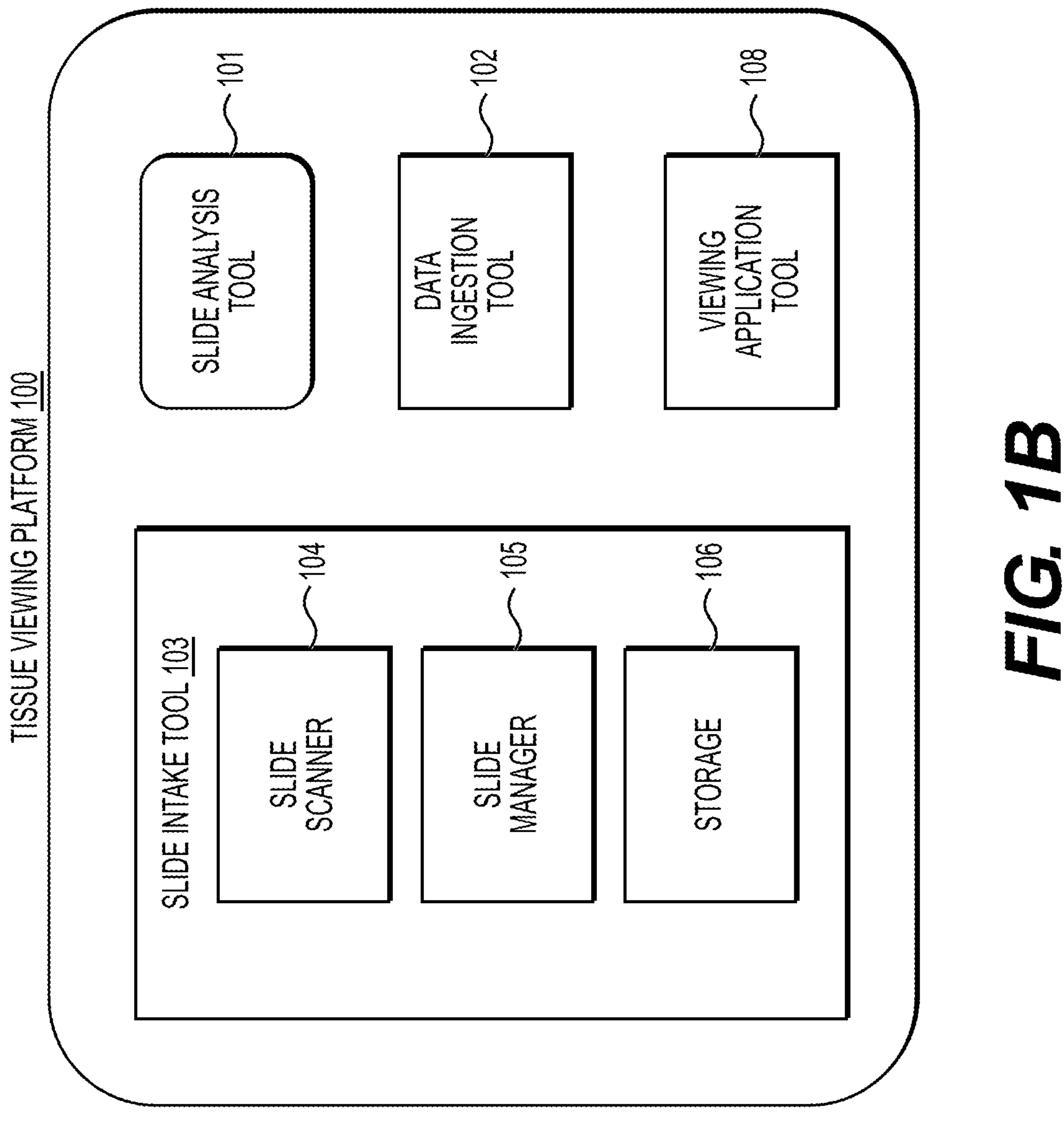
FIG. 1B illustrates an exemplary block diagram of a tissue viewing platform according to techniques presented herein.

FIG. 1B illustrates an exemplary block diagram of a tissue viewing platform 100 for determining specimen property of image property information pertaining to digital pathology image(s), using machine learning. For example, the tissue viewing platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen, and using machine learning to analyze a slide, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
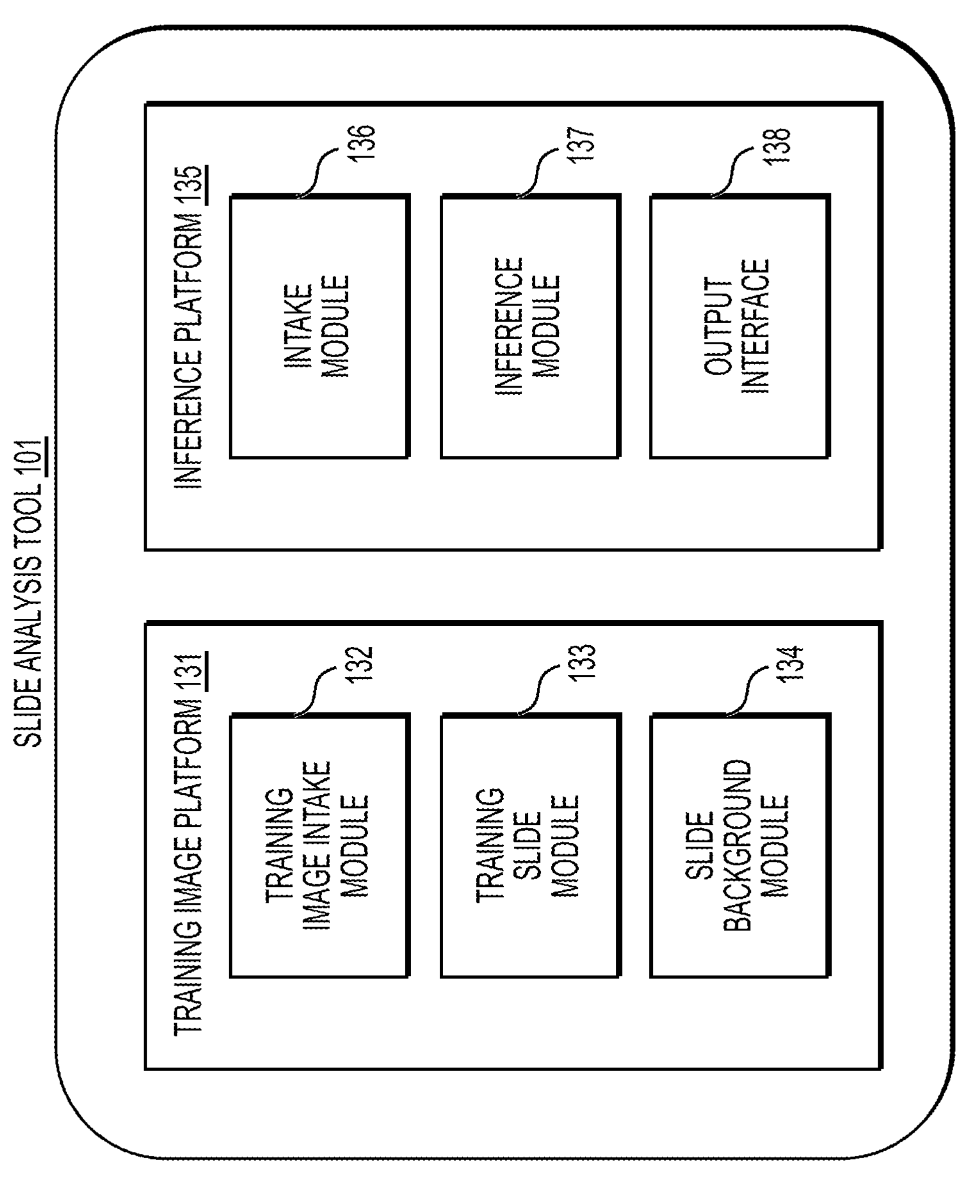
FIG. 1C illustrates an exemplary block diagram of a slide analysis tool, according to techniques presented herein.

FIG. 1C illustrates an exemplary block diagram of a slide analysis tool 101, according to an exemplary embodiment of the present disclosure. The slide analysis tool may include a training image platform 131 and/or a inference platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human and/or animal tissue and images that are graphically rendered. For example, the training images may be received from any one or any combination of the server systems 110, physician servers 121, and/or laboratory information systems 125. This dataset may be kept on a digital storage device. The training slide module 133 may intake training data that includes images and corresponding information. For example, training slide module 133 training data may include receiving one or more images (e.g., WSIs) of a human or animal. Further, the training data may include receiving a gross description (see. FIG. 2). Further, the intake module may receive information such as age, ethnicity, and ancillary test results. The training data may also include biomarkers such as genomic/epigenomic/transcriptomic/proteomic/microbiome information can also be ingested, e.g., point mutations, fusion events, copy number variations, microsatellite instabilities (MSI), or tumor mutation burden (TMB). The training slide module 133 may intake full WSIs, or may intake one or more tiles of WSIs. The training slide module 133 may include the ability to break an inputted WSI into tiles to perform further analysis of individual tiles of a WSI. The training slide module 133 may utilize convolutional neural network ("CNN"), graph neural network ("GNN"), CoordConv, Capsule network, Random Forest Support Vector Machine, or a Transformer trained directly with the appropriate loss function in order to help provide training for the machine learning techniques described herein. The training slide module 133 may further train a machine learning system to infer gross description fields from medical images and further extract/predict the spatial location of the information and display said information on medical digital images. The slide background module 134 may analyze images of tissues and determine a background within a digital pathology image. It is useful to identify a background within a digital pathology slide to ensure tissue segments are not overlooked.

According to one embodiment, the inference platform 135 may include an intake module 136, an inference module 137, and an output interface 138. The inference platform 135 may receive a plurality of electronic images/additional information and apply one or more machine learning model to the received plurality of electronic images/information to extract relevant information and integrate spatial and orientation information for display on medical digital images. For example, the plurality of electronic images or additional information may be received from any one or any combination of the server systems 110, physician servers 121, hospital servers 122, clinical trial servers 123, research lab servers 124, and/or laboratory information systems 125. The intake module 136 may receive WSI's corresponding to one or more patients/individuals. Further, the WSI's may correspond to an animal. The intake module 136 may further receive a gross description relating to one or more WSI. The gross description may contain information about the size, shape, and appearance of a specimen based on an examination of a WSI. The intake module 136 may further receive age, ethnicity, and ancillary test results and biomarkers such as genomic/epigenomic/transcriptomic/proteomic/microbiome information can also be ingested, e.g., point mutations, fusion events, copy number variations, microsatellite instabilities (MSI), or tumor mutation burden (TMB). The inference module 137 may apply one or more machine learning models to a group of WSI and any additional information in order to extract relevant information and integrate spatial and orientation information for display on medical images. The inference module 137 may further incorporate the spatial characteristics of the salient tissue into the prediction.

The output interface 138 may be used to output information about the inputted images and additional information (e.g., to a screen, monitor, storage device, web browser, etc.). The output information may include information related to ranking causes of death. Further, output interface 138 may output WSI's that indicate locations/salient regions that include evidence related to outputs from inference module 137.

The present disclosure describes how artificial intelligence (AI)/machine learning (ML) may be used to extract information from electronically stored data or metadata, such as from a gross description. This extraction may be used to display/output the extracted information on a digitized slide image to provide context for a pathologist, to provide additional layers of meaning to AI outputs (such as cancer detection), and/or to map the locations of sections taken relative to grossly removed organs or to radiological images.

Methods and systems disclosed herein may infer or determine gross description fields from medical images. The disclosed methods and systems may predict these gross description fields using spatial and/or color characteristics of a medical image. The system described herein may be capable of displaying inferred gross description fields onto relevant sections of digital medical images. The disclosed methods and systems may be applicable to both human and veterinary pathology (i.e., the system can be applied to digital images of humans and/or animals).

Methods and systems disclosed herein may describe how to use AI to interpolate and integrate information from different formats (e.g., text, image, genetics, etc.) from disparate sources of a pathology report and to further display the results to the pathologist allowing for histo-spatial correlation, and potentially radiologic-genomic correlation.

FIG. 2 illustrates an exemplary gross description according to an exemplary embodiment of the present disclosure. This may be an example of a gross description 201 that the system described herein can receive, process, and display on digital medical images. A gross description 201 may include a physical description of tissue taken during a biopsy. Information on the gross description may include specimen type, date and time that specimen was excised, weight, measurements, skin ellipses, nipple measurements (e.g., for a breast tissue), axillary tail, ink code information, sectioning, information on number of slices, needle-localization wire/radioactive seed, lesion information, distance between lesions, other findings, etc. The system described herein may be capable of receiving the gross description 201 similar to the example in FIG. 2. The system, as described may be capable of receiving one or more reports and extracting the metadata for further use (e.g., displaying the information on medical slide images).

Figure 3:
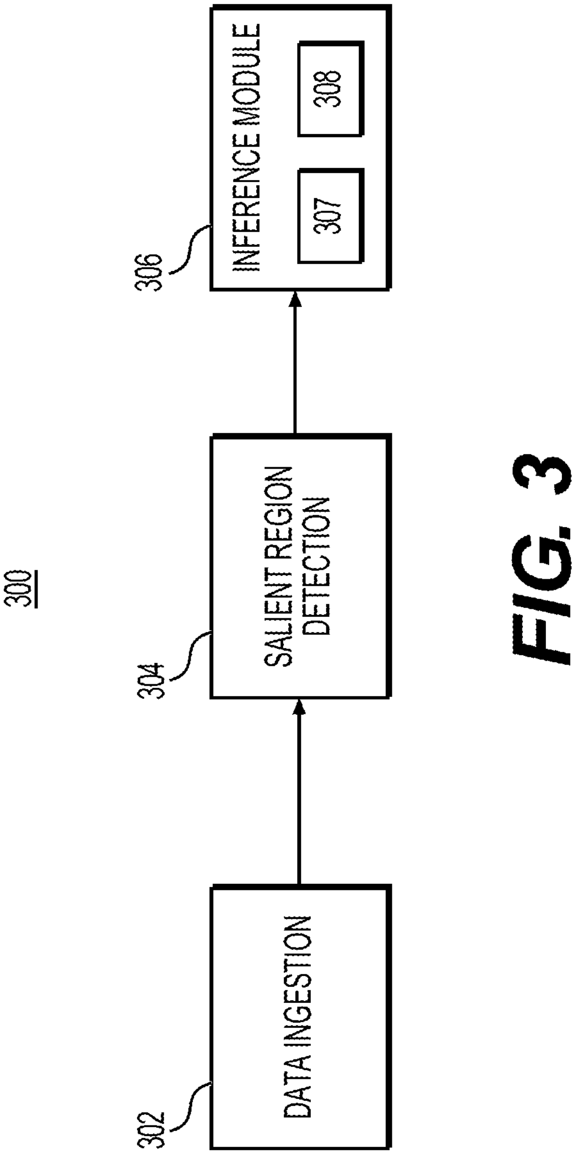
FIG. 3 illustrates a process for integrating gross description information onto a digital image, according to techniques presented herein.

FIG. 3 illustrates a process for integrating gross description information onto a digital image, according to techniques presented herein. Methods and systems disclosed herein may include data ingestion, salient region detection, and gross description inference as further described in FIG. 3. The system described in FIG. 3 may be performed by the slide analysis tool 101.

In FIG. 3, the system may first include data ingestion 302. Data Ingestion 302 may include receiving one or more digital medical images such as whole slide images (WSI) of a pathology specimen, magnetic resonance imaging (MRI) images, computed tomography (CT) images, positron emission tomography (PET) images, mammogram images, etc. These digital medical images may be received into a digital storage device 109 (e.g., hard drive, network drive, cloud storage, RAM, etc.) Optionally, patient information (e.g., age, ethnicity, ancillary test results, etc.) may also be received into the digital storage device 109. Further, a gross description may be received into digital storage 109. Each image may be paired with information from a gross description to train a machine learning system.

Next, data ingested may be inserted into a salient region detection module 304 as described in greater detail below. A salient region detection module 304, as further described below, may be used to identify the salient regions to be analyzed for each digital image. A salient region may be defined as an image or area of an image that is considered relevant to a pathologist performing diagnosis of an image. A digital image may be divided into patches/tile and a score may be associated with each tile, wherein the score indicates how relevant a particular tile/patch is to a particular task. Patches/tiles with scores above a threshold value may then be considered salient regions. In one example, a salient region of a slide may refer to the tissue areas, in contrast to the rest of the slide, which may be the background area of the WSI. One or more salient regions may be identified and analyzed for each digital image. This detection may be done manually by a human or automatically using AI. An entire image, or alternatively specific regions of an image, may be considered salient. The salient regions may be identified by one or more software modules. Salient region determination techniques are discussed in U.S. application Ser. No. 17/313,617, which is incorporated by reference herein in its entirety.

Next, the digital whole slide images from the data ingestion 302, which may or not have had a salient region identified, are fed to a inference module 306. The inference module 306 may have two sub-modules within it, the gross description inference module 307 and the spatial inference module 308. Within the gross description inference module 307, one or more fields in the gross description may be inferred using machine learning and/or computer vision from the digital image(s). Additionally, the spatial inference module 308 may incorporate spatial information from disparate regions in an image. Either the inferred information from gross description inference module 307 or inputted information from the gross description may be mapped to and displayed onto relevant locations of corresponding WSIs for viewing by a user (e.g., a pathologist). The inference, or prediction, is output to an electronic storage device.

The salient region detection module 304 and the inference module 306 are elaborated in greater detail below.

As discussed above, a salient region detection module 304 may be utilized prior to the system extracting information from a gross description and mapping the information. Each WSI may be divided into tiles or patches. The tile or patches may each include a continuous score of interest determined by the salient region detection module 304. The continuous score of interest may represent the saliency/relevancy of that area for a particular task. A continuous score of interest may be specific to certain structures within a digital image, and identifying relevant regions and excluding irrelevant regions may be important. For example, with MRI, PET, or CT, data localizing a specific organ of interest could be important for analysis and/or diagnosis. For histopathology, the continuous score of interest may be exhibited by an invasive tumor, a stroma around an invasive tumor, a lymphovascular space, an in-situ tumor, etc. Irrelevant regions may make up the majority of the image. Salient region identification may enable a downstream machine learning system to learn how to detect biomarkers from less annotated data and to make more accurate predictions.

A salient region detection module 304 or a salient region detector may output a salient region that was specified by a human annotator using an image segmentation mask, a bounding box, line segment, point annotation, freeform shape, or a polygon, or any combination of the aforementioned. Alternatively, this salient region detection module 304 may be created using machine learning to identify the appropriate locations.

There may be two general approaches to using machine learning to create a salient region detection module. The first approach may be a strongly supervised method that identifies precisely where a biomarker may be found. The second approach may be a weakly supervised method that does not provide a precise location.

For strongly supervised training, the system may use one or more images and one or more locations of salient regions that could potentially express the biomarker as an input. For two-dimensional (2D) images, e.g., whole slide images (WSI) in pathology, these locations could be specified with pixel-level labeling, bounding box-based labeling, polygon-based labeling, or by using a corresponding image where the saliency has been identified (e.g., using immunohistochemistry or IHC). For 3D images (e.g., CT and MRI scans), the locations could be specified with voxel-level labeling, by using a cuboid, etc. or by using a parameterized representation allowing subvoxel-level labeling, such as parameterized curves or surfaces, or a deformed template.

For weakly supervised training, the system may use one or more images and information regarding a presence or absence of salient regions, but exact locations of the salient location might not need to be specified.

FIG. 4A is a flowchart illustrating an example of how to train an algorithm for salient region detection module 304, according to techniques presented herein. The processes and techniques described in FIG. 4A may be used to train a machine learning model to identifier salient regions of medical digital images. The method 400 of FIG. 4A depicts steps that may be performed by, for example, training image platform 131 of slide analysis tool 101 as described above in FIG. 1C. Alternatively, the method may be performed by an external system.

Flowchart/method 400 depicts training steps to train a machine learning model as described in further detail in steps 402-406. The machine learning model may be used to identify salient regions of digital medical images as discussed further below.

At step 402, the system (e.g., the training image intake module 132) may receive one or more digital images of a medical specimen (e.g., from histology, CT, MRI, etc.) into a digital storage device (e.g., hard drive, network drive, cloud storage, RAM, etc.) and receive an indication of a presence or absence of a salient region (e.g., invasive cancer present, LVSI, in situ cancer, etc.) within the one or more images.

At step 404, each digital image may be broken into sub-regions that may then have their saliency determined. Sub-regions may be specified in a variety of methods and/or based on a variety of criteria, including creating tiles of the image, segmentations based on edge/contrast, segmentations via color differences, segmentations based on energy minimization, supervised determination by the machine learning model, EdgeBoxes, etc.

At step 406 a machine learning system may be trained that takes as input a digital image and predicts whether the salient region is present or not. Training the salient region detection module may also include training a machine learning system to receive, as an input, a digital image and to predict whether the salient region is present or not. Many methods may be used to learn which regions are salient, including but not limited to weak supervision, bounding box or polygon-based supervision, or pixel-level or voxel-level labeling.

Weak supervision may involve training a machine learning model (e.g., multi-layer perceptron (MLP), convolutional neural network (CNN), transformers, graph neural network, support vector machine (SVM), random forest, etc.) using multiple instance learning (MIL). The MIL may use weak labeling of the digital image or a collection of images. The label may correspond to the presence or absence of a salient region.

Bounding box or polygon-based supervision may involve training a machine learning model (e.g., R-CNN, Faster R-CNN, Selective Search, etc.) using bounding boxes or polygons. The bounding boxes or polygons may specify sub-regions of the digital image that are salient for detection of the presence or absence of a biomarker.

Pixel-level or voxel-level labeling (e.g., semantic or instance segmentation) may involve training a machine learning model (e.g., Mask R-CNN, U-Net, fully convolutional neural network, transformers, etc.) where individual pixels and/or voxels are identified as being salient for the detection of continuous score(s) of interest. Labels could include in situ tumor, invasive tumor, tumor stroma, fat, etc. Pixel-level/voxel-level labeling may be from a human annotator or may be from registered images that indicate saliency.

FIG. 4B is a flowchart illustrating methods for how to provide image region detection, according to one or more exemplary embodiments herein. FIG. 4B may illustrate a method that utilizes the neural network that was trained in FIG. 4A. The exemplary method 450 (e.g., steps 452-456) of FIG. 4B depicts steps that may be performed by, for example, by inference platform 135 of slide analysis tool 101. These steps may be performed automatically or in response to a request from a user (e.g., physician, pathologist, etc.). Alternatively, the method described in flowchart 450 may be performed by any computer process system capable of receiving image inputs such as device 1400 and capable of including or importing the neural network described in FIG. 4A.

At step 452, a system (e.g., intake module 136) may receive one or more digital medical images may be received of a medical specimen into a digital storage device (e.g., hard drive, network drive, cloud storage, RAM, etc.). Using the salient region detection module may optionally include breaking or dividing each digital image into sub-regions and determining a saliency (e.g., cancerous tissue for which the biomarker(s) should be identified) of each sub-region using the same approach from training step 404.

At step 454, the trained machine learning system from FIG. 4A may be applied to the inputted images to predict which regions of the one or more images are salient and could potentially exhibit the continuous score(s) of interest (e.g., cancerous tissue). Applying the trained learning system to the image may include expanding the region or regions to additional tissue, such as by detecting an invasive tumor region, determining its spatial extent, and extracting a stroma around the invasive tumor.

At step 456, if salient regions are found at step 454, the system may identify the salient region locations and flag them. If salient regions are present, detection of the region can be done using a variety of methods, including but not restricted to: running the machine learning model on image sub-regions to generate the prediction for each sub-region; or using machine learning visualization tools to create a detailed heatmap, etc. Example techniques are described in U.S. application Ser. No. 17/016,048, filed Sep. 9, 2020, and Ser. No. 17/313,617, filed May 6, 2021, which are incorporated herein by reference in their entireties. The detailed heatmap may be created by using class activation maps, GradCAM, etc. Machine learning visualization tools may then be used to extract relevant regions and/or location information.

The outputted salient regions from step 456, may then be fed into the inference module 306. The inference module 306 may predict a gross description or parts of a gross description, while incorporating spatial characteristics of the salient regions or tissue into the prediction (e.g., using the gross description inference module 307). Further, the inference module 306 may be capable of mapping data from the gross description to specific WSIs and further displaying this information on WSIs (e.g., using the spatial inference module 308). Further, the spatial inference module 308 may be capable of predicting the most relevant location on the WSI to display extracted descriptions. There may be two primary ways to create a spatial inference module 308 that uses spatial characteristics include using an end-to-end system and/or using a two-stage prediction system. The end-to-end system may be trained directly from an input image, whereas the two-stage system may first extracts features from the image and then use machine learning methods that may incorporate a spatial organization of the features. The training of the inference module 306 may be described in greater detail below. Examples of training the inference module 306 may include method 500 of FIG. 5A. Examples of using the inference module 306 may include method 550 of FIG. 5B.

Figure 5A:
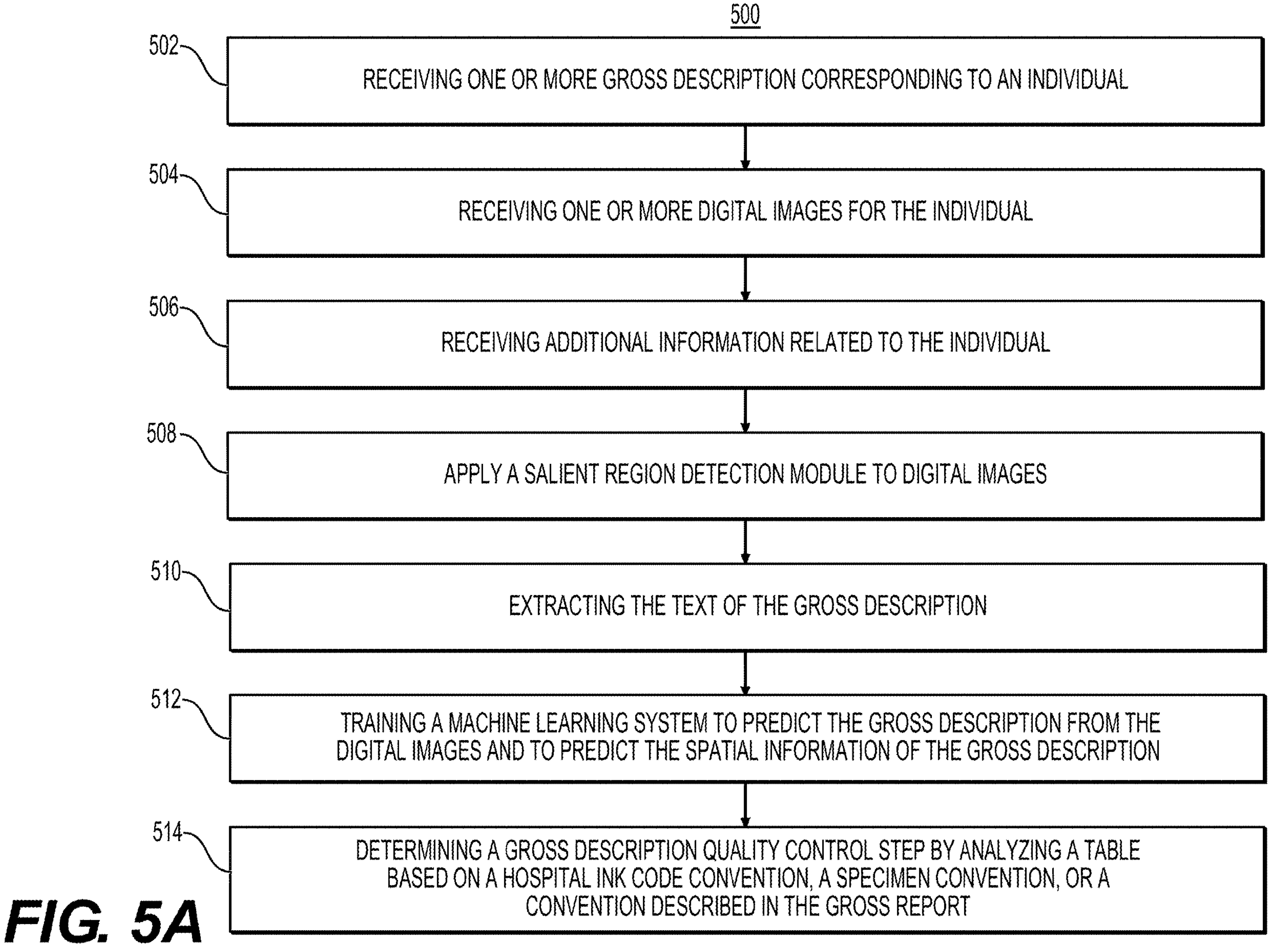
FIG. 5A is a flowchart illustrating an example method for training an algorithm for integrating gross description information on a slide, according to techniques presented herein.

FIG. 5A is a flowchart illustrating an example of how to train an algorithm for integrating gross description information on a slide, according to techniques presented herein. The method 500 of FIG. 5A depicts steps that may be performed by, for example, training image platform 131 of slide analysis tool 101 as described above in FIG. 1C. Alternatively, the method 500 may be performed by an external system.

At step 502, the system (e.g., the training image platform 131), may receive one or more gross descriptions (e.g., the gross description of FIG. 2). The gross description may be either an electronically documented text paragraph stored into a digital storage device 109 (e.g., hard drive, network drive, cloud storage, RAM, etc.) and accessed via the anatomic pathology laboratory information system 125 (AP-LIS). The gross description may describe one or more inputted WSI (e.g., WSIs inputted at step 504). The gross description may include information that corresponds the information from the gross description to a WSI and a radiological image. This spatial information may be utilized for training the machine learning system.

At step 504, the system (e.g., the training image intake module 132) may receive one or more digital images of slides for a patient into a digital storage device 109 (e.g., hard drive, network drive, cloud storage, RAM, etc.). In particular, the system may receive WSI and radiologic images corresponding to one or more patients. The received one or more digital images may be images that correspond to the gross description and not necessarily all images in a patient or case file. Each image may be paired with information from the gross description to train the machine learning system. Each image and specimen that is imaged may have a corresponding gross description and summary of section/grossing legend. These documents may describes the organs and findings within those organs (e.g., the gross description) as well as which pieces of those organs were submitted for histologic exam, were made into WSIs (e.g., the summary of sections/grossing legends). The grossing legend/summary of sections may be a list of what tissue from the entire gross specimen is submitted for histologic exam. For example, a large part of a patient's colon might be removed because the patient has colon cancer. The pathology assistant who receives the colon may first describe it and type that description into a corresponding gross description (e.g., it is X cm long and has a tumor Y cm from the edge of the colon etc.). The pathologist assistant may then cut pieces out of the colon for further examination by a pathologist under a microscope (e.g., a piece from the tumor). The gross legend may state, for example: block or slide 17=piece of tumor to describe the location of slide/specimen.

At step 506, training module 306 (e.g., both the gross description inference module 307 and the spatial inference module 308) may optionally include ingesting or receiving patient information such as age, ethnicity, ancillary test results, etc. to stratify and split the system for machine learning. Training the gross description prediction module may also optionally include ingesting or receiving biomarkers such as genomic, epigenomic, transcriptomic, proteomic, and/or microbiome information. This information may include, for example, point mutations, fusion events, copy number variations, microsatellite instabilities (MSI), and tumor mutation burden (TMB).

At step 508, training the inference module 306 may also optionally include using the salient region detection module 304 to identify a saliency of each region within the one or more images and to exclude non-salient image regions from subsequent processing.

At step 510, training the inference module 306 may include training a machine learning or configuring a rule-based system to extract the text of the gross description of the tissue (e.g., for the gross description inference module 307). The machine learning system may capture data about size, texture, color, shape, lesions, landmarks, and distances. The machine learning system may use Natural Language Processing (NLP) systems such as encoder-decoder systems, Seq2Seq, and/or Recurrent Neural Networks to extract a structured form of the gross description. Given a structured gross description, a rule-based text extraction system may be used. For example, FIG. 2 is an example structured gross description. If the system received the gross description of FIG. 2. The system may then be capable of using rule-based text extraction to receive the information from the gross description. For instance, the rule-based text extraction may be able to export the text input for each of the predefined fields and save this data to a database (e.g., storage devices 109) for further use. Further, the system may be capable of associating all extracted data with a particular patient and/or a particular slides or set of slides from step 502.

At step 512, training the inference module 306 may include training the machine learning system to predict the gross description fields from salient image regions. Gross description fields may be represented as ordinal values, integers, real numbers, etc. For fields in the gross description such as anterior, posterior, lateral, medial, superior, and/or inferior orientation, the system may be trained with a multi-class cross-entropy loss. For fields in the gross description such as measurements in distances such as centimeters (cm), weight (grams/ounces), or percentages (e.g., a percentage of fibrous tissue), the system may be trained using a regression loss (e.g., mean squared error loss, Huber loss, etc.), an ordinal loss function, or a counting loss function (e.g., Poisson regression loss, negative binomial regression loss, etc.). To incorporate the spatial information (e.g., training the spatial inference module 308), coordinates of each pixel/voxel may optionally be concatenated to each pixel/voxel. Alternatively, the coordinates may optionally be appended throughout processing (e.g., using the CoordConv algorithm). In one embodiment, by providing the overall system with training slides and a corresponding gross description, the system may be trained to identify the gross description values. This may be done by analyzing the WSI using the techniques described above, while also training the system to identify the spatial locations of the gross description and teaching the system how to map the gross description data to the relevant locations on one or more types of images. These images may include a WSI or radiologic image. In one embodiment, when training the system (e.g., the spatial inference module 308) to identify the location of slides within a radiologic image, the input to the system used may be a pathology WSI, the radiology image and/or the gross description. The system may directly learn the XY location of the WSI on the radiology image. Alternatively or additionally, the radiology image may be pre-annotated e.g. pixelwise labeled or region of interest for each organ present in the radiology image. From the gross description the organ type and the measurements of the organ may be extracted (size etc.). From the WSI the overall size of the tissue can be taken, etc., using a salient tissue extractor, which may mark the tissue area in combination with the slide metadata (magnification level, microns per pixel). With the WSI size and optionally the gross description, the size and orientation of box 604 (described in greater detail below) can be determined.

As another alternative, the machine learning algorithm may passively take spatial information into consideration by self-selecting regions in the input (e.g., section of the inputted WSIs) to process. In one embodiment, the system may receive a single gross description and multiple WSI inputs that correspond the gross description in steps 502-504. The select selected regions may be edge regions for example, where ink is present. For example, in one WSI the edge region may be from the lateral side, and the next WSI may be from the Medial area. If patient information (e.g., age) and or genomic, epigenomic, transcriptomic, proteomic, and/or microbiome information is also used as an input, in addition to medical image data, then that information may be input into the machine learning system as an additional input feature. Machine learning systems that may be trained include, but are not limited to, a convolutional neural network ("CNN"), CoordConv, Capsule network, Random Forest, and/or Support Vector Machine trained directly with an appropriate gross description fields prediction loss function.

At step 514, training the inference module 306 may optionally include a gross description quality control step. If the gross description is missing, or as a supplement to the gross description, a table based on a hospitals ink code convention, a specimen convention (e.g., mastectomy), or a convention described in the gross description may be used as an additional automated quality control step. If the ink code convention is physically stored, training the gross description prediction module may optionally include a manual process step to digitally capture information from the ink code convention and store it into a digital storage device (e.g., hard drive, network drive, cloud storage, RAM, etc.).

In a gross room, a specimen may be painted according to its anterior, posterior, lateral, medial, superior, and/or inferior orientation. Given a hospital's color code, a presence of paint detected from one of these regions may also be reported. One rule-based mechanism may involve an assignment of a linkage via color coding which may crosscheck data from the gross description. One AI-based system may use the above description system to detect any ink that remained on a hematoxylin and eosin stained histology slide. Based on the detected ink, the system may use a lookup table of the hospital and determine from which area or location that tissue on the H&E slide originated. The location may be displayed to the pathologist on the slide. Furthermore, these locations may be used to automatically cross-check the gross description and/or the gross description. An example lookup table appears below. The AI system may detect ink, which is mapped to a hospital's tissue definition (ink code), which is then displayed digitally to a pathologist.

| Ink color | Hospital 1 specimen/ gross description | Hospital 2 specimen/ gross description |
|---|---|---|
| Black | Lateral | Posterior |
| Blue | Medial | Superior |
| Green | Inferior | Inferior |
| Red | Superior | Medial |
| Orange | Superficial | Lateral |
| Yellow | Anterior | Anterior |

Figure 5B:
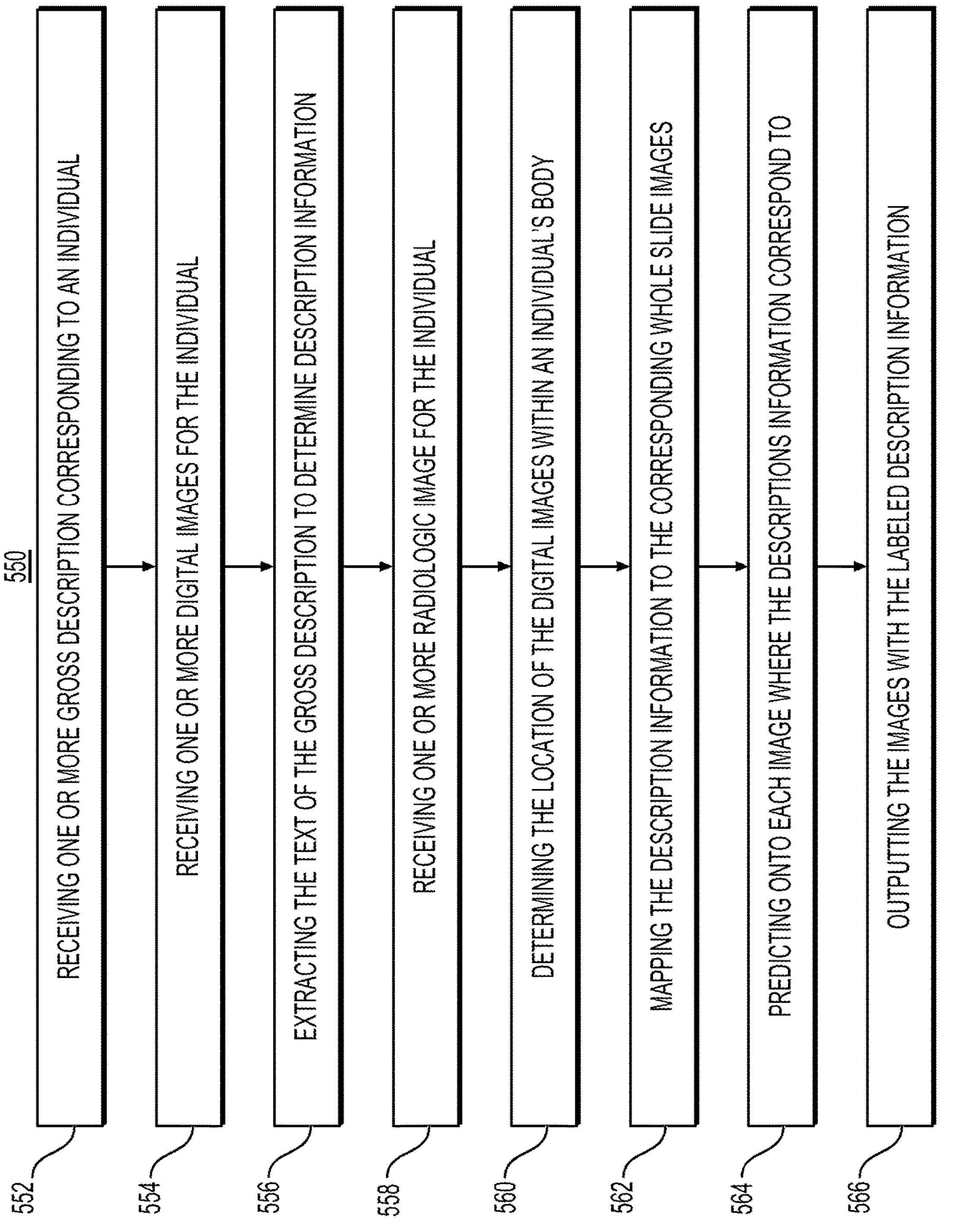
FIG. 5B is a flowchart illustrating exemplary methods for integrating gross description information onto a corresponding slide, according to one or more exemplary embodiments herein.

FIG. 5B is a flowchart illustrating exemplary methods for determining gross report information from a slide and/or integrating gross description information onto a slide, according to one or more exemplary embodiments herein. The exemplary method 550 (e.g., steps 552-566) of FIG. 5B depicts steps that may be performed by, for example, by inference platform 135 of slide analysis tool 101. These steps may be performed automatically or in response to a request from a user (e.g., physician, pathologist, etc.). These steps may describe an exemplary method of how to use the trained system described in FIG. 5A. Alternatively, the method described in flowchart 550 may be performed by any computer process system capable of receiving image inputs such as device 1400 and capable of including or importing the neural network described in FIG. 5A.

At step 552, the system (e.g., the intake module 136) may receive one or more gross descriptions from a patient into a digital storage device 109 (e.g., hard drive, network drive, cloud storage, RAM, etc.). The gross description may include information about one or more WSIs and further define the location of slides with respect to one another.

At step 554, the system (e.g., the intake module 136) may receive one or more digital images of pathology specimens from a patient (e.g., histology, cytology, etc.) into a digital storage device 109 (e.g., hard drive, network drive, cloud storage, RAM, etc.). The digital images received may each correspond to the gross descriptions received at step 552. The gross description may provide information that describes physical aspects of the slides that were received at step 554.

Step 556 may utilize techniques described in step 510 to extract data from the imported gross description from step 552.

Figure 6:
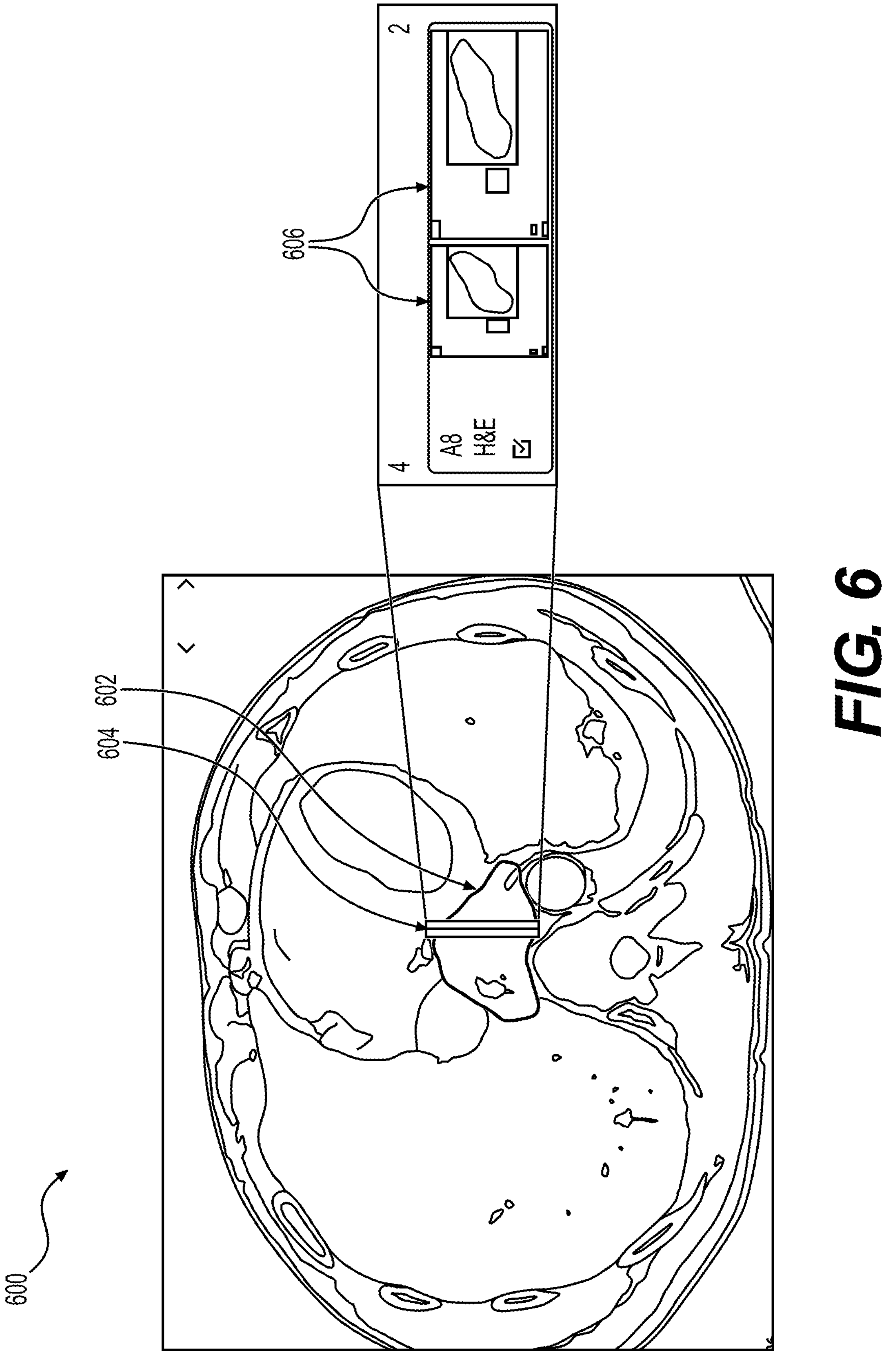
FIG. 6 illustrates a histologic slide and an indication of its general presence in a radiologic image.

At step 558, the system (e.g., the inference module 137) may receive or determine one or more radiologic image that corresponds to one or more slides from step 552. The radiologic image may be stored into a digital storage device 109 (e.g., hard drive, network drive, cloud storage, RAM, etc.). The system may be capable of using a radiologic slide 600 as a base image to output to a user. The area of interest in a radiologic slide 600 may defined by a bounding box 602. The bounding box 602 may describe an area in a radiologic slide 600 where tissue samples were previously extracted from. The area where a particular WSI was extracted from may be referred to as the "sample location." These previously extracted tissues may be the tissue samples located within the images received at step 552. The bounding box 602 may be created by a user at this step. Further, the salient region detection module 304 may be capable of creating the bounding box 602. Within the bounding box 602 may be one or more forms of marking 604 that identifies where particular WSIs were created from (i.e., the sample locations). In one example, the markings 604 may be dashes or extended rectangles. The system may be capable of determining the location of markings 604 by using the information extracted at step 556. In another embodiment, the system may be capable of determining the markings 604 by analyzing inputted WSIs and radiologic image from step 552. The system may thus be capable of depicting the location of inputted slides in a corresponding radiologic slide 600. Further, the system may be capable of allowing for a user to view one or more digital images 606 besides the radiologic slide 600 by selecting one or more markings 604. This may allow for a user of the system to have a better understanding of the location of all inputted slides 606 in relation to one another and within a particular patient's body. When the radiologic image is displayed, a histologic slide (e.g., a WSI) may be oriented, and its general presence in a radiologic image may be displayed, as shown in FIG. 6. FIG. 6 shows an example orientation of a histologic slide and may display its general presence in a radiologic image. The system may further me capable of mapping WSI to other 2D images or 3D images as described in further detail below.

At step 560, the system (e.g., the intake module 136) may further receive location information from a Computed Tomography (CT) scan, Magnetic Resonance Imaging (MRI), Ultrasound, Positron Emission Tomography and/or Mammography. The system may be capable of inputting those images/scans directly, or may be capable of receiving information based on the images or scans. The additional inputted information may include information as to which slide/slides with which the input corresponds. The system may thus be capable of receiving further detailed information on the location of the inputted images from 552. With location information from the Computed Tomography (CT) scan, Magnetic Resonance Imaging (MRI), Ultrasound, Positron Emission Tomography and/or Mammography, in addition to the gross description, the system may be capable of locating the two-dimensional or three-dimensional location of the inputted WSIs from step 552.

At step 562, the system (e.g., the inference module 137) may be capable of using an AI system to map data from the gross description to specific WSIs to which the information pertains. At this step, if no gross description has been inserted at step 552, the system may utilize the gross description inference module 307 to infer this information by analyzing the inserted WSIs from step 554. At this step, the AI system trained in FIG. 4A may be capable of determining what information from the gross description is relevant to each inputted WSI from step 554. The system may then label each piece of information received (e.g., the information extracted from the gross description) as relevant or not relevant for each inputted WSI from step 552. Further, the system may use the trained AI system from FIG. 5A to display, on each WSI, a location as extracted from a 'legend' of the gross description.

At step 564, the system (e.g., the spatial inference module 308) may use the AI system from FIG. 5A to predict onto each inputted WSI from step 552, where the location of certain descriptions are (e.g., the "associated location"). The associated location may be the most relevant visual output on a WSI that depicts the extracted data. For example, for measurement of a cancer tissue, the system may label the x, y measurement information along an x, y dimensions of the cancer within a WSI. Accordingly, some or all information extracted from the gross description at step 556 and any gross description information inferred at step 560 from the gross description inference module 307 may be labeled onto their corresponding WSIs. For example, the measurement of a nipple and a skin ellipses and the description may be inputted onto a WSI. Wherever this predictive imaging is not possible, or does not make sense, the prediction is simply displayed as a written description near the whole slide image. For instance, the system may label certain general information such as specimen type, date/time excides, date/time into formalin, and weight onto the corner of a WSI to provide additional information for a pathologist to see when examining a WSI. These updated slides may be saved with additional information labeled onto them.

At step 564, the trained system may include a quality control step where the system may cross check the prediction of the mapped gross description information with a description stored in an anatomic pathology laboratory information system (APLIS). Discrepancies may be highlighted in the gross description and highlighted on the WSI via XY coordination and/or a heatmap. If any discrepancies are determined, the system may output a notification (e.g., an email) describing the discrepancy to an individual.

At step 566, the system (e.g., the output interface module 138) may display the WSI with the additional information to a user (e.g., a pathologist) (e.g., pathologist), and/or save the information to electronic storage. The system may also output a larger system image/three-dimensional figure such as radiologic image 600 or a 3d image (as described in FIG. 7). This system image or figure may be capable of including the inputted WSIs at the corresponding sample locations. The WSIs may include description information from the associated gross descriptions. This information may be displayed, immediately, or once a user (e.g., a pathologist), selects a particular WSI from a sample location. This may allow for a user (e.g., a pathologist), to click between different WSIs, while seeing the mapped data from the gross description and also being able to visualize the location of the WSIs within a body.

In one embodiment, the system (e.g., the spatial inference module 308) may be capable of situating a gross resected specimen within one or more histopathology images. Situating a gross resected specimen within histopathology images may include using a detailed specimen, tumor and distance-to-margin measurements of a gross description, and/or information from radiation therapy. These measurements and information may be used as coordinates to situate the gross resected specimen within any available imaging files/data. Additionally, using a grossing legend, the system may map the digitized slides to the location within the gross specimen and consequently, within the imaging file. This mapping may also help locate slides in relation to where therapy was targeted. For example, therapy may have been given to a patient prior to a resection of the corresponding organ. This tissue may then show signs of therapy that can be visualized under a microscope and may be apparent for an individual utilizing the system described herein.

Figure 7:
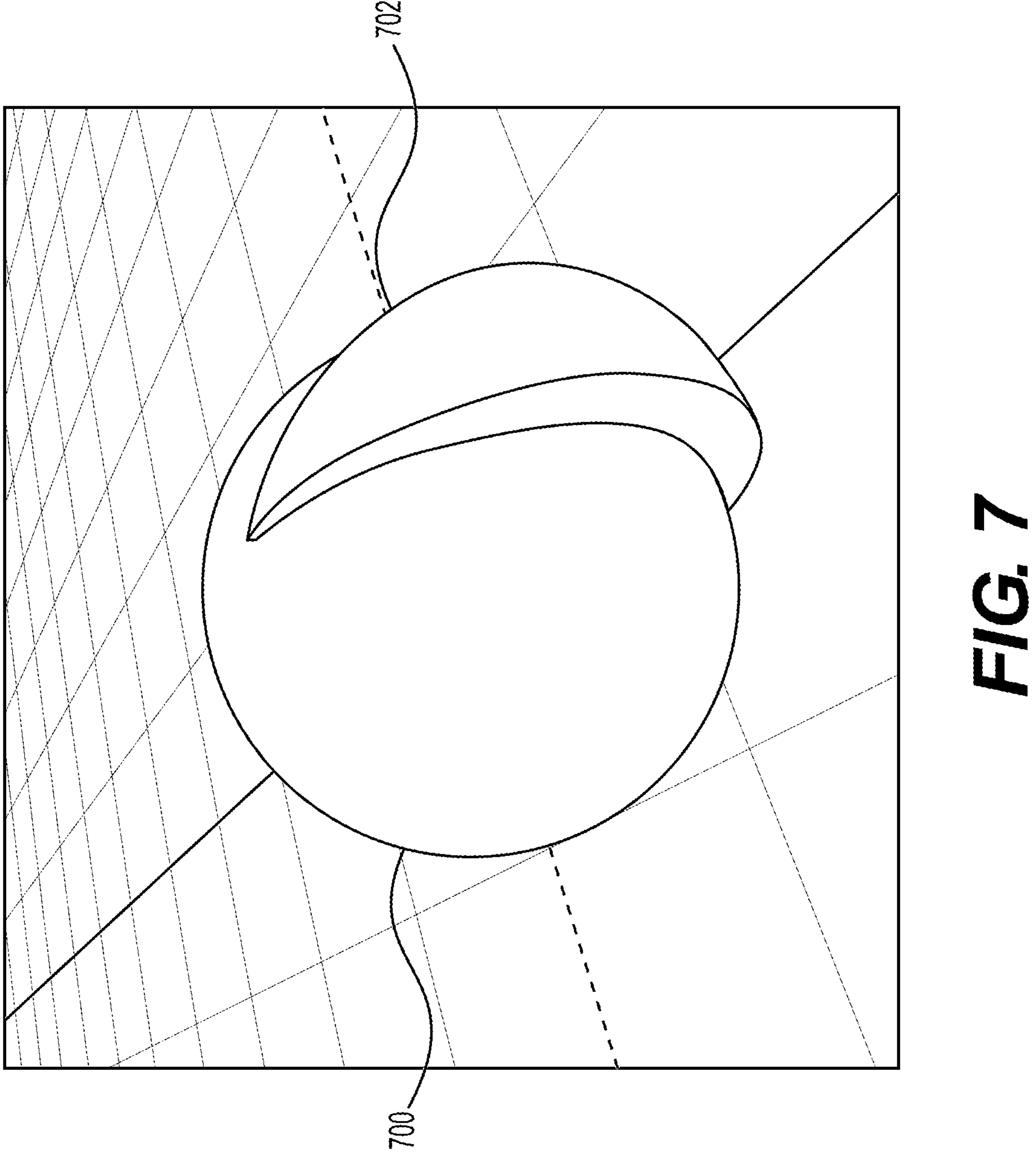
FIG. 7 illustrates a three-dimensional exemplary visualization for breast tissue.
Figure 8:
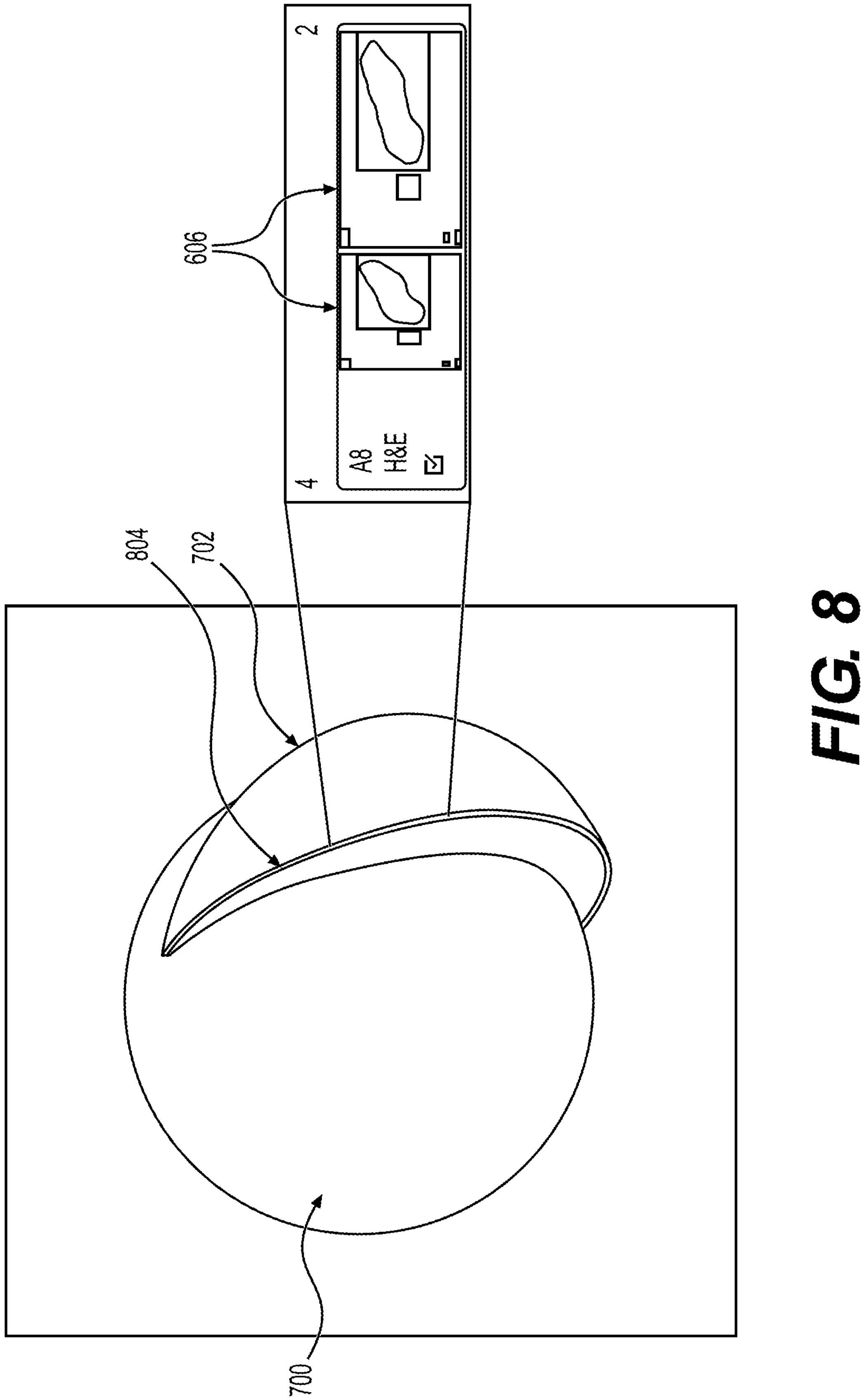
FIG. 8 illustrates one or more histologic slide on a three-dimensional exemplary visualization for breast tissue.

Subsequently, all of the slides (e.g., the slides inputted at step 552 corresponding to a single patient) may be oriented/displayed in relation to where they came from in the gross specimen. This embodiment may allow for a user (e.g., pathologist) to potentially not need to refer to the grossing legend to understand the site from which the one or more slides were created. This system may allow quick visual display of the sites being sampled across the resection specimen and potentially allow the pathologist to relate findings seen on one slide to findings in adjacent nearby slides. In a viewing platform, a single button may display these sampled sites. FIG. 6 may display an example of this embodiment. Further, FIG. 7 may provide another example of this embodiment. FIG. 7 shows an exemplary embodiment of a breast tissue 700 as a three-dimensional model. Given an excision of a breast tissue 700 (gray sphere) or other tissue, a visualization may display whether a particular WSI tissue slide 702 is on a margin, lateral, medial, inferior, and/or anterior area and where in 3D space this piece of tissue lies. The system may be capable of showing multiple WSI 702 on a single tissue 700. As another example of this embodiment, FIG. 8 illustrates one or more histologic slides on a three-dimensional exemplary visualization for breast tissue. Within FIG. 8, a single WSI 804 is shown on the three-dimensional specimen 700. Similar to FIG. 6, the slices themselves may be selected by selecting a slice a marking that represents the slice. This may allow for the corresponding WSI 606 with inputted data to be displayed to the pathologist. The corresponding WSI 606 may include information mapped onto the slide based on the gross description or gross description as described in FIG. 5B.

In another embodiment, the system (e.g., the spatial inference module 308) may be capable of quantifying a tumor in three linear dimensions (x, y, z). This embodiment may depict an example of step 562 of FIG. 5B and be performed by the spatial inference module 308. One of the dimensions may be calculated by adding an amount of tumor on consecutive slides. When multiple slides are located next to one another and all have a tumor at the same (x,y) direction, then the z dimension may be calculated by adding the distance between all consecutive slides that contain a tumor at an x, y location. The x, y location may be determined by the system measuring the x, y distance of a tumor at various WSIs. This x, y information may be available to the system once the measurement information is extracted from the gross description and/or inferred from the inputted WSIs. Furthermore, because gross description measurements and potentially radiographic measurements may be extracted according to the methods and systems disclosed herein (e.g., at steps 556-560), all these measurements may be correlated. For example, the tumor may have previously been measured by palpation, by radiology, by gross exam of the tissue, and measurement by histologic exam. If the tumor measurement differs significantly from a radiographic or gross measurement at slides located next to one another, such difference might indicate a need for further sampling. In such a case, a message might be sent to a user (e.g., pathologist or grossing assistant/pathology assistant) via a secure email, hospital notification system, etc. This message may provide information such as the location of a desired additional sample.

In another embodiment, the system (e.g., the inference module 306) may be capable of predicting formalin fixation time. Formalin fixation time may refer to the period of time between when a tissue is placed in formalin to when the tissue is processed. Tissue being processed may entail the following steps: removing the tissue from the formalin, grossing the tissue (i.e., writing a gross description, selecting pieces of tissue to submit for histologic exam), dehydrating the pieces of tissue selected in paraffin blocks, cutting the tissue from the paraffin block, and placing the cut tissue-paraffin slice onto a slide to then be stained with hematoxylin and eosin for histologic exam. Within this embodiment, the system may use this additional piece of information as another piece of data to be displayed onto a WSI at step 564.

Figure 9A:
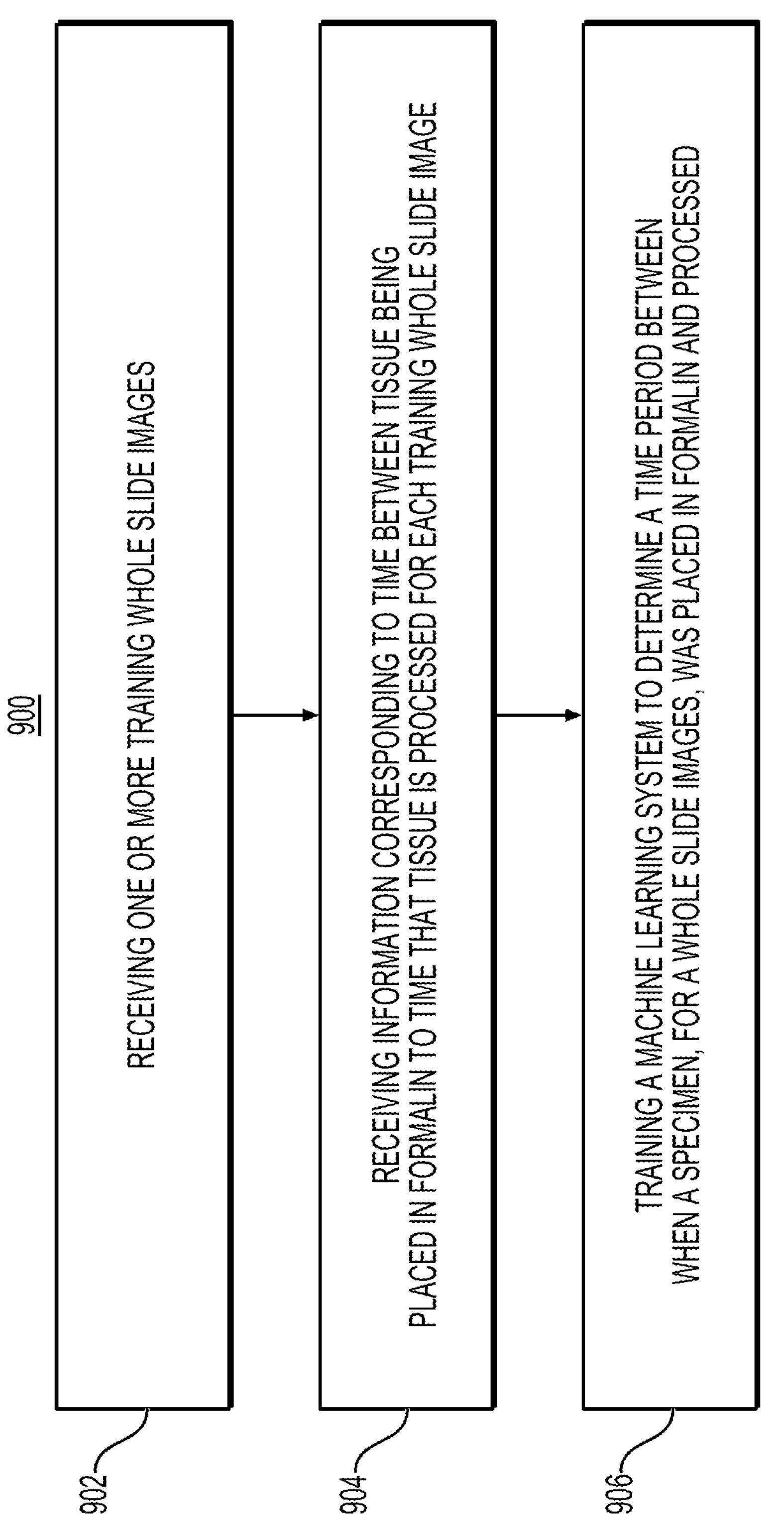
FIG. 9A is a flowchart illustrating an example method for training an algorithm to determine the time between when a specimen was placed in formalin and processed, according to techniques presented herein.

FIG. 9A is a flowchart illustrating how to train an algorithm for determining time between when a specimen was placed in formalin and processed, according to techniques presented herein. The method 900 of FIG. 9A depicts steps that may be performed by, for example, training image platform 131 of slide analysis tool 101 as described above in FIG. 1C. Alternatively, the method 900 may be performed by an external system.

Flowchart/method 900 depicts training steps to train a machine learning module as describe in further detail in steps 902-906.

At step 902 the system (e.g., the intake module 136) may receive digital images (e.g., H&E whole slide images) of pathology specimens from a human/animal may be received into a digital storage device (e.g., hard drive, network drive, cloud storage, RAM, etc.).

At step 904 the system (e.g., the intake module 136) may receive information corresponding to the amount of time between the tissue being placed in formalin to the time that tissue is processed for each training whole slide image inserted at step 902.

At step 906, the system (e.g., training slide module 133) may be used to train a machine learning system to predict the time between when tissue is placed in formalin to when the tissue is processed. This embodiment (e.g., the system described in FIGS. 9A and 9B) may be a function of the gross description inference module 307. Training may include using multiple instance regression to train a machine learning system to determine a time between when tissue is placed in formalin.

The trained machine learning system may then be saved with the updated parameters to digital storage 109.

Figure 9B:
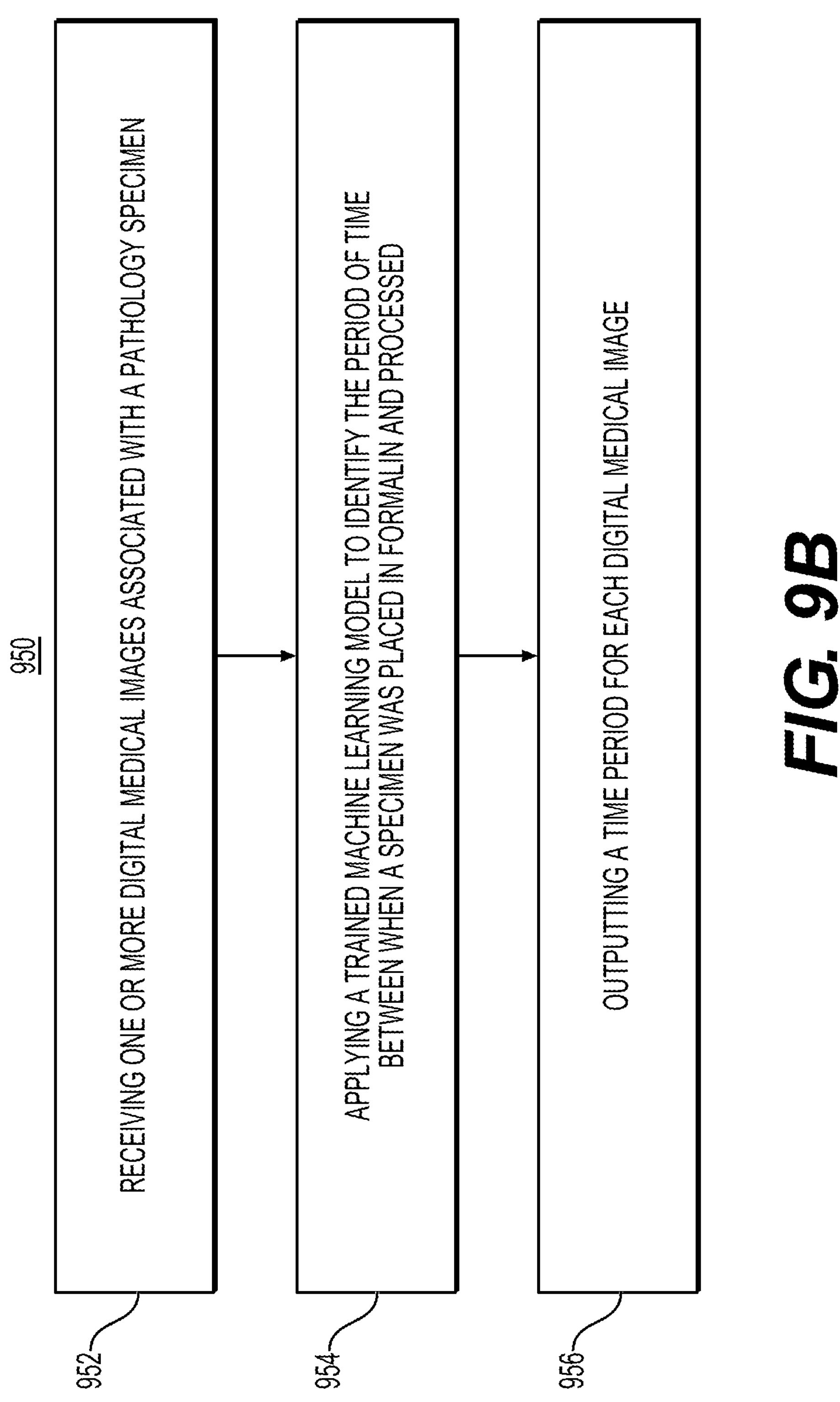
FIG. 9B is a flowchart illustrating an exemplary methods for determining the time between when a specimen was placed in formalin and processed, according to one or more exemplary embodiments herein.

FIG. 9B is a flowchart illustrating an exemplary method for determining time between when a specimen was placed in formalin and processed, according to one or more exemplary embodiments herein. The exemplary method 950 (e.g., steps 952-556) of FIG. 9B depicts steps that may be performed by, for example, by inference platform 135 of slide analysis tool 101. These steps may be performed automatically or in response to a request from a user (e.g., physician, pathologist, etc.). Alternatively, the method described in flowchart 950 may be performed by any computer process system capable of receiving image inputs such as device 1400 and capable of including or importing the neural network described in FIG. 9A.

At step 952 the system (e.g., the intake module 136 of slide analysis tool 101) may receive digital images (e.g., H&E whole slide images) of pathology specimens from a human/animal may be received into a digital storage device (e.g., hard drive, network drive, cloud storage, RAM, etc.).

At step 954, the system (e.g., the inference module 137) may apply the trained machine learning module from FIG. 9A to the slides inputted at step 952. The trained machine learning module may then be capable of determining a time period as an output.

At step 956, the time for each image may be stored to digital storage 109 or outputted to a user. In addition, the predicted formalin fixation time may also be used as a QC (Quality Control) step for the overall system. Here, the system may automatically notify a hospital information system (HIS) or laboratory information management system 125 (LIMS) whether formalin fixation was insufficient and/or whether the tissue was degraded in ways in which the pathologist or technician must be notified. For example, poorly fixed tissue might result in poor stain update or autolysis change. The system may optionally notify involved individuals on their mobile devices and send digital documents or messages in regard to the gross description.

Results of hormonal biomarkers (e.g., estrogen receptor (ER), progesterone receptor (PR), and her2), genomic biomarkers, proteomic biomarkers, and microbiome markers may be affected by the formalin fixation time. When these biomarkers are detected, the formalin fixation time may be received into downstream biomarker modules as a correction input such that the results of these biomarkers may be outputted in the context of formalin fixation time.

In another embodiment, the system (e.g., the inference module 306) may be capable of predicting tissue ischemic time. Tissue ischemic time may refer to the period of time between when a tissue is removed from a patient and placed in formalin. Within this embodiment, the system may use this additional piece of information as another pace of data to be displayed onto a WSI at step 564.

Figure 10A:
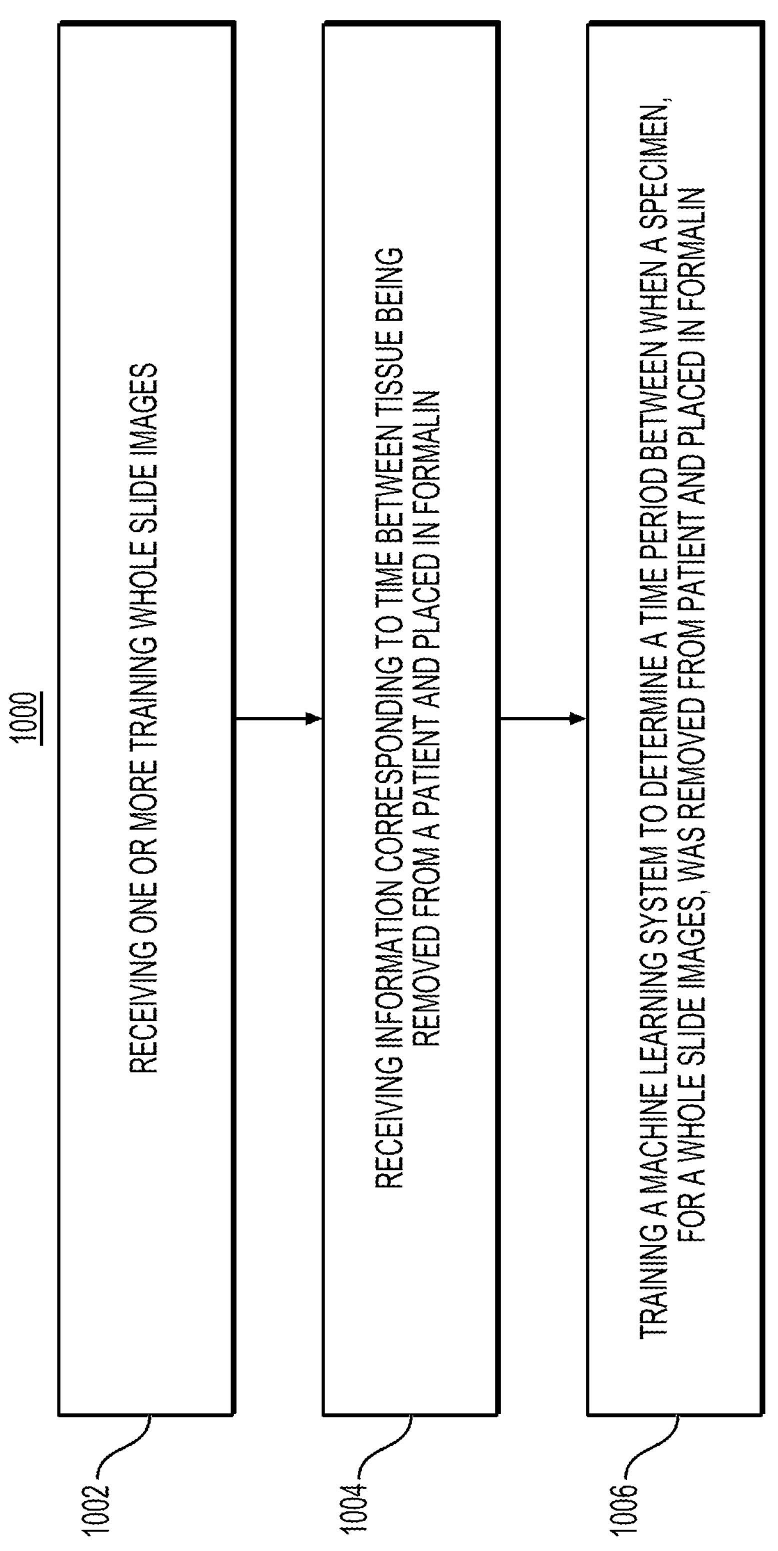
FIG. 10A is a flowchart illustrating an example method for training an algorithm to determine the time between when a specimen was removed from specimen and placed in formalin, according to techniques presented herein.

FIG. 10A is a flowchart illustrating an exemplary method of how to train an algorithm for determining time between when a specimen was removed from specimen and placed in formalin, according to techniques presented herein. The method 1000 of FIG. 10A depicts steps that may be performed by, for example, training image platform 131 of slide analysis tool 101 as described above in FIG. 1C. Alternatively, the method 1000 may be performed by an external system.

Flowchart/method 1000 depicts training steps to train a machine learning module as describe in further detail in steps 1002-1006.

At step 1002 the system (e.g., the intake module 136 of slide analysis tool 101) may receive digital images (e.g., H&E whole slide images) of pathology specimens from a human/animal may be received into a digital storage device (e.g., hard drive, network drive, cloud storage, RAM, etc.).

At step 1004, the system (e.g., the intake module 136) may receive information corresponding to the amount of time between tissue being removed from a patient and the time that tissue is placed in formalin for each training whole slide image inserted at step 1002.

At step 1006, the system (e.g., training slide module 133) may be used to train a machine learning system to predict the time between when tissue was removed from a body to when the tissue is placed in formalin. This embodiment (e.g., the system described in FIGS. 10A and 10B) may be a function of the gross description inference module 307. Training may include using multiple instance regression to train a machine learning system to predict the time between when tissue was removed from a body to when the tissue is placed in formalin.

The trained machine learning system may then be saved with the updated parameters to digital storage 109.

Figure 10B:
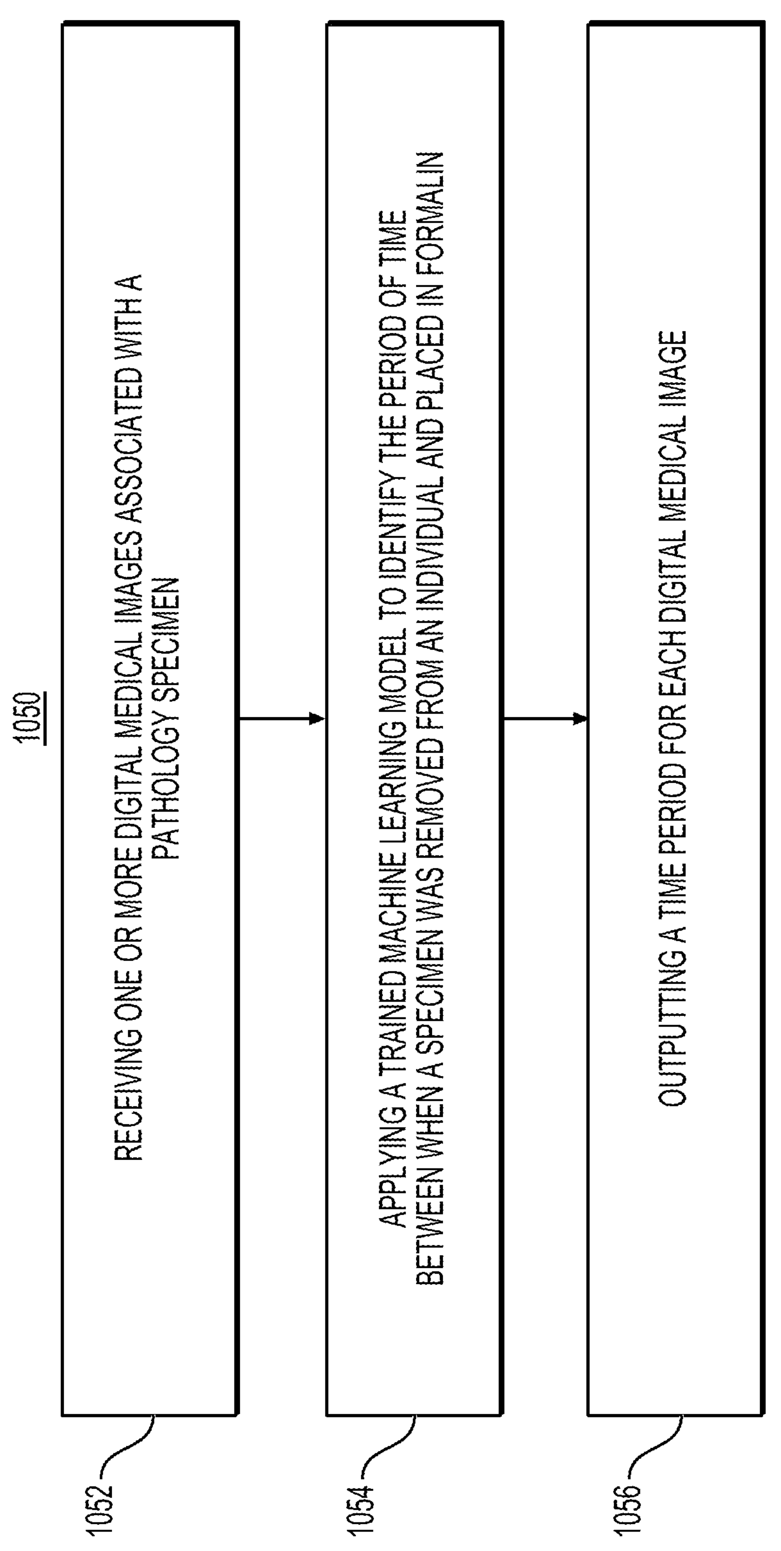
FIG. 10B is a flowchart illustrating exemplary methods for determining time between when a specimen was removed from specimen and placed in formalin, according to one or more exemplary embodiments herein.

FIG. 10B is a flowchart illustrating an exemplary methods for determining the time between when a specimen was removed from specimen and placed in formalin, according to one or more exemplary embodiments herein. The exemplary method 1050 (e.g., steps 1052-1056) of FIG. 10B depicts steps that may be performed by, for example, by inference platform 135 of slide analysis tool 101. These steps may be performed automatically or in response to a request from a user (e.g., physician, pathologist, etc.). Alternatively, the method described in flowchart 1050 may be performed by any computer process system capable of receiving image inputs such as device 1400 and capable of including or importing the neural network described in FIG. 10A.

At step 1052 the system (e.g., the intake module 136 of slide analysis tool 101) may receive digital images (e.g., H&E whole slide images) of pathology specimens from a human/animal may be received into a digital storage device (e.g., hard drive, network drive, cloud storage, RAM, etc.).

At step 1054, the system (e.g., the inference module 137) may apply the trained machine learning module from FIG. 10A to the slides inputted at step 1052. The trained machine learning module may then be capable of determining a time period as an output for each slide.

At step 1056, the time for each image may be stored to digital storage 109 or outputted to a user. This time may be a piece of information that the system as a whole outputs onto the WSI for when a user views the WSI. The system may be capable of notifying a pathologist or lab technician if an insufficient period of time is determined for any of the inserted whole slide images.

Figure 11A:
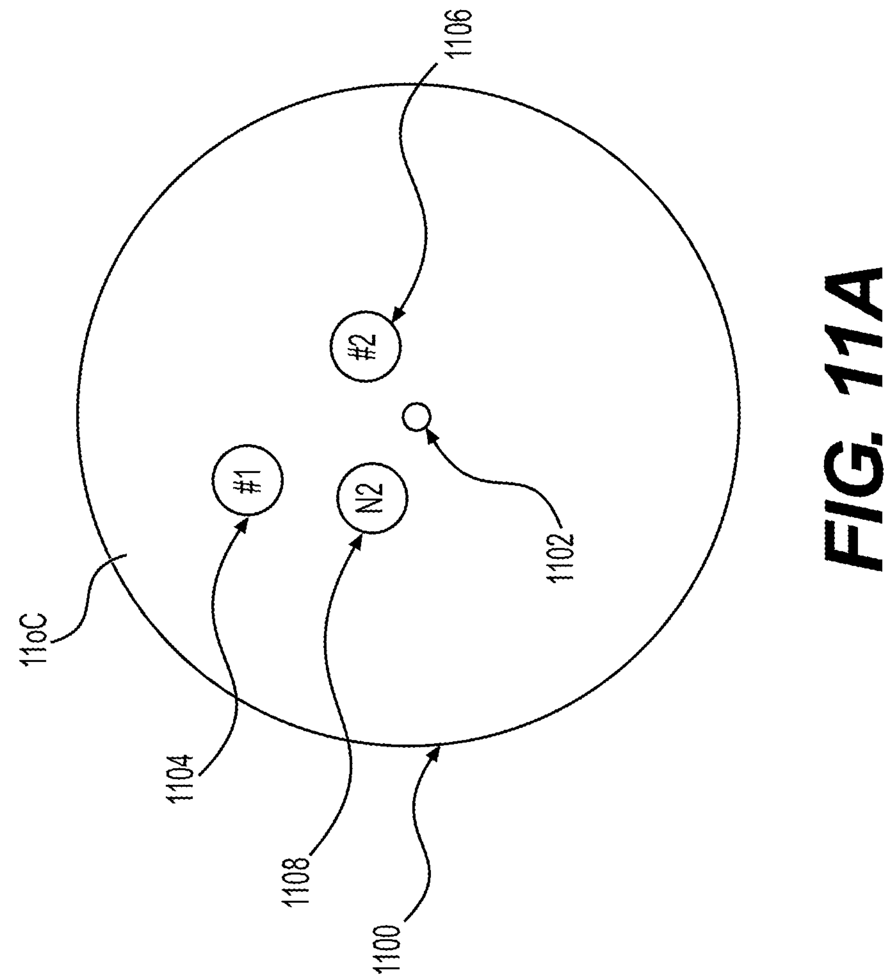
FIG. 11A illustrates a diagram of a woman's right breast from a front side.

In another embodiment, the system (e.g., the spatial inference module 308) may be capable inferring or determining an "o'clock" orientation or position of a WSI. The "o'clock" description may referred to an alternative coordinate system that is a convention used pathology that may correspond to angular positions of a circle. The system may be trained to extract information from a gross description related to location and to translate the coordinates. For instance, distance from nipple and additional information for a lesion may be translated by the system to provide updated geographical information for aspects of each slide (e.g., coordinates in a o'clock orientation). FIG. 11A illustrates a diagram of a woman's right breast from a front side, or as if a physician were examining the diagram of the breast. A central dot appearing in FIG. 11A may represent a nipple 1102. A notation "11oc" appearing in FIG. 11A may refer to an "11 o'clock" position, which may be similar to an angular position with respect to the dot. The breast may be approximated as a circular shape, and the circular shape of the breast may be divided circumferentially like clock hours (similar to degrees of a circle). The 11 o'clock position may be equivalent to 330 degrees clockwise if 0 degrees is located centrally at the top of the diagram. A distance of lesions relative to the nipple ("N") may be given in centimeters, such that in this diagram, "N2" 1108 may refer to a lesion that is ~2 cm from the nipple. The system described herein may be capable of receiving input information from a gross description to describe the relative location of the lesion N2 1108. The system may then use the inputted measurement information and output the coordinates based on the o'clock position and distance from the nipple. For example, N2 1108 may be output as located at 10 o'clock position at a distance of 2 cm. This additional information determined by the inference module 306 may then be labeled onto one or more relevant WSIs.

Abnormalities in female breasts may be detected by radiographic imaging (e.g., mammography, ultrasound, and MRIs). Whenever abnormalities are discovered by a physician (e.g., radiologist), those abnormalities may be described using characteristic descriptions and may be given locations or sites according to the above conventions (o'clock, distance from the nipple). These descriptions allow a physician to biopsy one or more lesions under imaging guidance and be confident that the one or more lesions are in a correct location when performing the biopsy. The biopsy may involve an insertion of a needle into tissue at the location. The needle may be hollow, and a core of tissue may be removed as the needle is extracted from the breast. As the needle is extracted, a miniscule piece of metal ("clip") may be placed at the location of the biopsy (and the location of the radiographic abnormality). This clip typically has a unique shape. The clip may be a very small barbell, may have a coil shape, or may be curvilinear. The location or placement of this clip may be used to visualize with further radiographic imaging, as metal may be readily imaged. In addition, if results of the biopsy require further excision of the abnormality, the location of the clip may guide a physician (e.g., surgeon) as to where to direct such additional excision. In cases of breast conserving surgery, the abnormality may be excised alone while a remainder of the breast may be left in place on the patient.

In the example shown in FIG. 11A, this patient had three abnormalities or lesions (1104, 1106, and 1108) detected in the breast, each of which was biopsied with a slightly different finding and each of which had a different clip placed at the biopsy site. The locations are designated by circles around N2 1108, #1 1104, and #2 1106. In the example, the patient underwent a right mastectomy where her entire breast was removed with all three lesions. Even before the breast appeared in pathology, the diagram in FIG. 11A was created as a map so that the physician may know what to expect when grossing the breast, or slicing the breast. When grossing, the physician knew, from the map, to look for three somewhat dispersed and somewhat close masses or legions with miniscule clips within them. The information used to create the map in FIG. 11A was obtained from radiology reports and subsequent biopsy report results that followed after abnormal radiology reports prompted biopsy. The system described in FIG. 5B, specifically the spatial inference module 308, may be capable of producing this figure and outputting the image (e.g., at step 566). The output itself may be an image of the gross organ or cartoon representation with the WSIs that are derived from certain parts of that organ layered on that cartoon image. For example, FIG. 11A, would be an example of this cartoon output of a gross breast specimen and have a certain number of slides over site labeled "#2" that come from that part of the gross organ.

Upon grossing the breast, the physician sampled each of these three lesions to confirm that there was cancer at each site and to determine a type and grade of the cancer. These determinations may be very important to staging of the patient and therefore to treatment and prognosis of the patient.

Upon grossing the breast, the example gross description of FIG. 11B was generated. A part of the gross description within the gross description may describe a size of the breast, a size of the skin overlying the breast, and a size of the nipple, as well as any orienting sutures that would help a physician tell which side of the specimen was lateral, superior, medial, or inferior. Additional sections (the third section is abbreviated in FIG. 11B) may describe the three lesions or masses that were mapped out FIG. 11A. Each lesion (e.g., 1104, 1106, and 1108) may have a site or orientation, a size, a brief description, a description of a clip that was found at the site, and a distance of the site to relevant landmarks (e.g., margins, the nipple, and the other two sites of the two other lesions).

When sections are taken from each of these sites, if these sections are observed under a microscope by a physician, the physician may have no way of knowing from where that tissue is taken. The only way for the physician to know where the tissue was taken may be to look at a legend, key, or summary of sections at the end of the gross description. FIG. 11C shows an example "summary of sections" along with an inking code, which may be referred to collectively as a legend.

This legend may allow the physician to understand that if the physician is observing, under the microscope, a slide cut from, for example, block E, the physician may know that this slide contains a section from the 11:00 o'clock mass. If the physician is observing a slide cut from block P, the physician may know that this slide contains a section from a central biopsy site. Details such as these might seem trivial but are important in integrating much information from diagnosis to biomarkers that might have clinical impact. However, continuously referring to this legend and back to the microscope may be burdensome.

Systems and methods disclosed herein may create an AI system that would be able to display, on the whole slide image, information found in the summary of sections in text form, and would be very helpful. Systems and methods disclosed herein may also display whole slide images or thumbnails of those whole slide images on a contextual map of tissue, whether it be radiographic or gross. Systems and methods disclosed herein may also integrate this displayed map with ink color and margins to provide another layer of contextual information. As different genomic information extracted from different blocks becomes available, this mapping might also prove crucial to data integration.

In another embodiment, the system (e.g., the inference module 306) may be capable inferring or determining whether a site or location of a previous biopsy (as indicated by a clip placement generating "biopsy site change") was sampled in a resection specimen. This may be an exemplary use of step 562. The embodiment may include a machine learning model being trained to detect changes in tissue that occurred from a previous biopsy. This inference may ensure that the site of a previous diagnosis is visualized.

In another embodiment, the system (e.g., the inference module 306) may be used to analyze multiple disparate tumors.

Figure 12A:
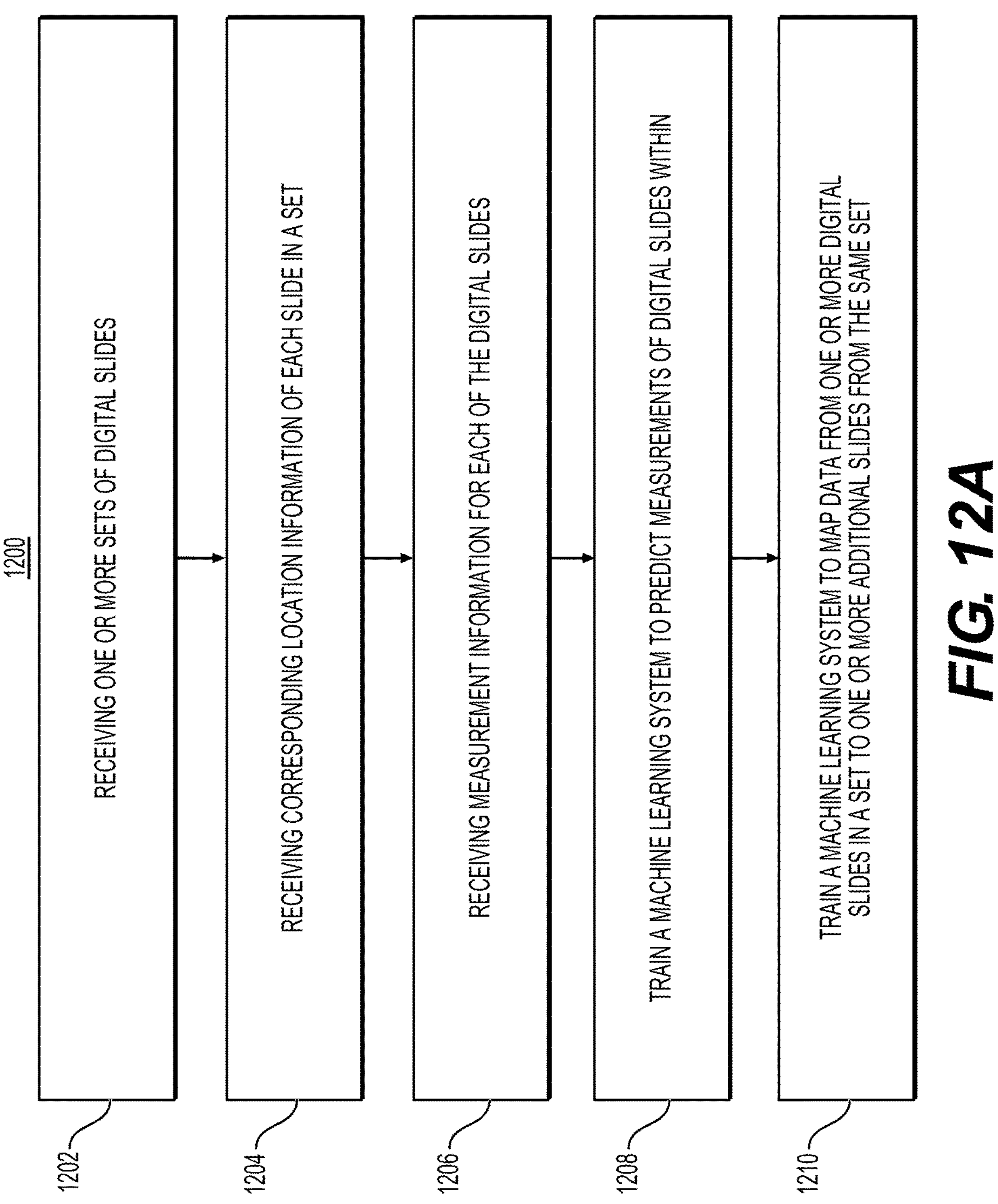
FIG. 12A is a flowchart illustrating an exemplary method for training an algorithm to map data from one or more digital slides to another digital slide, according to techniques presented herein.
Figure 12B:
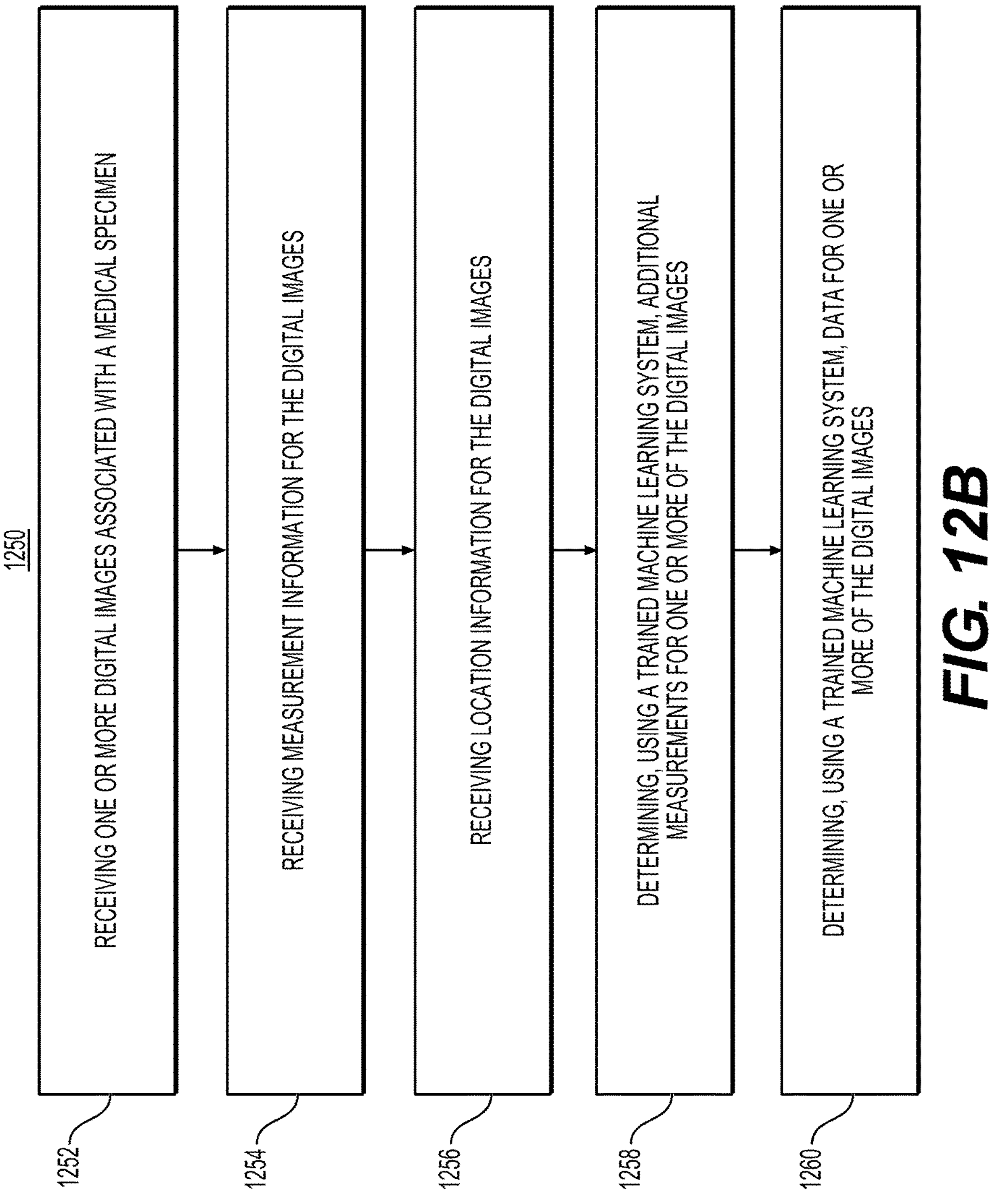
FIG. 12B is a flowchart illustrating exemplary methods for mapping data from one or more digital slides to another digital slide, according to one or more exemplary embodiments herein.

The embodiment of FIG. 12A or 12B may take place at step 552, 558, or 562 from FIG. 5B. If the tumors are in different organs, then this step may occur at step 552 because each organ may have its own description. If the tumors are in the same organ, this may occur at step 558 or 562 where radiology and gross information would dictate the location of the tumors from within the organs.

FIG. 12A is a flowchart illustrating an exemplary method for training an algorithm to map data from one or more digital slides to another digital slide, according to techniques presented herein. The method 1200 of FIG. 12A depicts steps that may be performed by, for example, training image platform 131 of slide analysis tool 101 as described above in FIG. 1C. Alternatively, the method 1200 may be performed by an external system.

Flowchart/method 1200 depicts training steps to train a machine learning module as describe in further detail in steps 1202-1210.

At step 1202 the system (e.g., the training image intake module 132) may receive digital images (e.g., H&E whole slide images) of pathology specimens from a human/animal may be received into a digital storage device (e.g., hard drive, network drive, cloud storage, RAM, etc.).

At step 1204, the system (e.g., the training image intake module 132) may receive information describing the location of all inputted slides from step 1204. This information may be received from a gross description or independently inserted. This information may include information related to the physical distance between all slides and the slides orientations. Further, the information may describe which slides are located next to one another.

At step 1206, the system (e.g., the training image intake module 132) may receive measurement information for multiple genomic, transcriptomic, proteomic or microbiomic measurements associated with each of the input slides (e.g., H&E slides) from step 1202.

At step 1208, the system (e.g., the training slide module 133) may train a machine learning module to predict measurements of the inserted digital slides. Measurement information may include any physical measurements that are described in the gross description at FIG. 2. For example, the measurement may be the x, y length of a particular tumor. This may be done by training the machine learning module to determine measurement information for slide A. For example, slide A may be located between slides B and C. The system may be able to utilize measurement information from slides B and C inputted at step 1206, combined with additional locational information at step 1204 to train a machine learning module to predict measurements for slide A. In another embodiment, slide A may be generated by a GAN.

The training used at step 1208 may include using a multiple instance regression approach. Alternatively, a regression system in which the measurements were previously manually labeled for the system to train on may be used.

The measurement in step 1208 may be used to place slides positionally and predict their location. Then, based on this location derived from the measurement, we step 1210 may be performed, which would provide more information about the tissue. For example, if tissue A and B are from two separate tumors measured 10 cm apart, and tissue C is 5 cm from A and 5 cm from B, then we know that tissue C is between A and B from step 1208. If A and B are tumor tissue that are truly distinct and separate, then we can use step 1210 to predict that the tissue from C is normal, non-tumor tissue At step 1210, the system (e.g., the spatial inference module 308) may train a machine learning module to map data from one or more digital slides in a set to one or more additional slides form the same set. Set may refer to one or more slides located adjacent to one another. The system may be trained utilizing a CNN, transformer, or GNN. The system may be trained similar to step 1208 to use the data from surrounding slides to determine and map additional data onto slides.

FIG. 12B is a flowchart illustrating exemplary methods for mapping data from one or more digital slides to another digital slide, according to one or more exemplary embodiments herein. The exemplary method 1250 (e.g., steps 1252-1256) of FIG. 12B depicts steps that may be performed by, for example, by inference platform 135 of slide analysis tool 101. These steps may be performed automatically or in response to a request from a user (e.g., physician, pathologist, etc.). Alternatively, the method described in flowchart 1250 may be performed by any computer process system capable of receiving image inputs such as device 1400 and capable of including or importing the neural network described in FIG. 12A.

At step 1252 the system (e.g., the intake module 136) may receive digital images (e.g., H&E whole slide images) of pathology specimens from a human/animal may be received into a digital storage device (e.g., hard drive, network drive, cloud storage, RAM, etc.).

At step 1254 and 1256, the system (e.g., the intake module 136) may further receive measurement information and location information for each of the inputted slides. This information may correspond to the information received at steps 1204 and 1206. In this embodiment, some of the inputted slides may not have corresponding measurement information.

At step 1258, the system (e.g., the inference module 137) may apply the trained machine learning module from step 1208 to inputted slides to determine additional measurement information for one or more inputted WSI based on the surrounding slides. If one of the inserted slides is not measured with one of these technologies but lies in proximity between slides that have been measured, measurements may be inferred or determined for this slide based on location, in addition to phenotypical presences. For example, given a transcriptomic measurement in right base and right apex locations, the transcriptomic profile of a mid-region may be estimated by the system.

At step 1260, the system (e.g., the inference module 137) may apply the trained machine learning module from step 1208 to the inputted slides to determine additional information for slides based on the surrounding slides. Because systems and methods disclosed herein may map sites sampled in glass slides to a location within the gross specimen, the disclosed systems and methods may also map any data derived from the slides to the location within the gross specimen. This mapped data (e.g., diagnostic, transcriptomic, genomic, proteomic etc.) may be used to predict data or parameters from other sample sites within an excision that lacks this data. For example, genomic data may be available for only two of three tumors within an excision. Systems and methods disclosed herein may integrate genomic data available on those two tumors with a physical location of those tumors in relation to the third, unstudied tumor, to infer or determine genomic or other characteristics about that tumor.

In another embodiment, the system (e.g., the inference module 306) may be used in Veterinary pathology. Example organisms or specimen may be horses (*Equus ferus caballus*) and dogs (*Canis lupus familiaris*). For example, when performing punch biopsies in dogs, a gross description may note information such as a location, size, extent, shape, contour, color, and texture. Using the AI system, the system may suggest, among other suggestions, whether the size and extent of the biopsy was sufficient.

Figure 13:
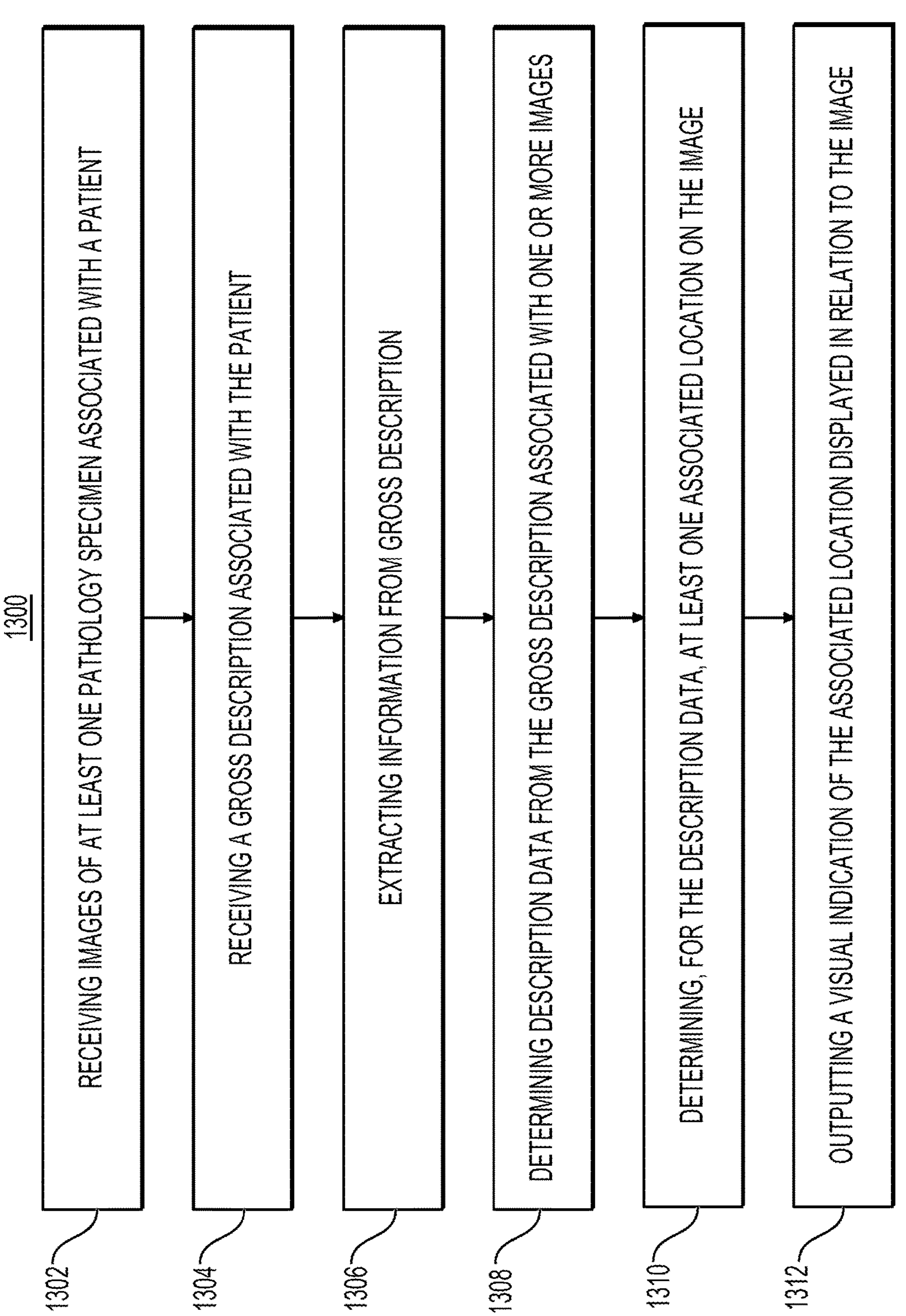
FIG. 13 is a flowchart illustrating methods for integrating gross description information onto a digital image, according to one or more exemplary embodiments herein.

FIG. 13 is a flowchart illustrating methods for determining how to integrate gross description information onto one or more corresponding slides. Flowchart 1300 may depict steps to utilize a trained machine learning module as described in further detail in steps 1302-1310.

At step 1302, the system (e.g., the image intake module 136) may receive images of at least one pathology specimen, the pathology specimen being associated with an individual/patient/animal.

At step 1304, the system (e.g., the image intake module 136) may receive a gross description, the gross description comprising data about the medical images.

At step 1306, the system (e.g., the inference module 137) may extract data from the gross description.

At step 1308, the system (e.g., the inference module 137) may determine, using a machine learning system, at least one associated location of the medical images for one or more pieces of data extracted.

At step 1310, the system (e.g., the output interface 138) may output a visual indication of the description data displayed in relation to the medical images.

In one embodiment, the system may further determine if the gross description is structured or unstructured, if the system determines that the gross description is structured, the system may provide the gross description a rule-based AI system. In contrast, if the system determines the gross description is unstructured, the system may provide the gross description to a natural language processing based machine learning system. The system may further receive a corresponding radiologic image associated with a patient and determine a sample location of the medical images relative to the radiologic image. The system may also include the ability to display the sample location of the medical image relative to the radiologic image. The system may further receive a corresponding three-dimensional figure associated with a patient and determine a sample location of the medical images relative to the three-dimensional figure. The system may also compare the associated location of the data on the medical images with an external system, wherein any discrepancies are marked. The system may further determine that diseased tissue is present in two or more of the plurality of medical images and determine a location of the diseased tissue in the three-dimensions based on the determined location of diseased tissue within the medial images. The system may also be capable of estimating an area and/or volume of the diseased tissue. The system may further determine a new coordinate system for measurement data of lesions within the medical images.

Figure 14:
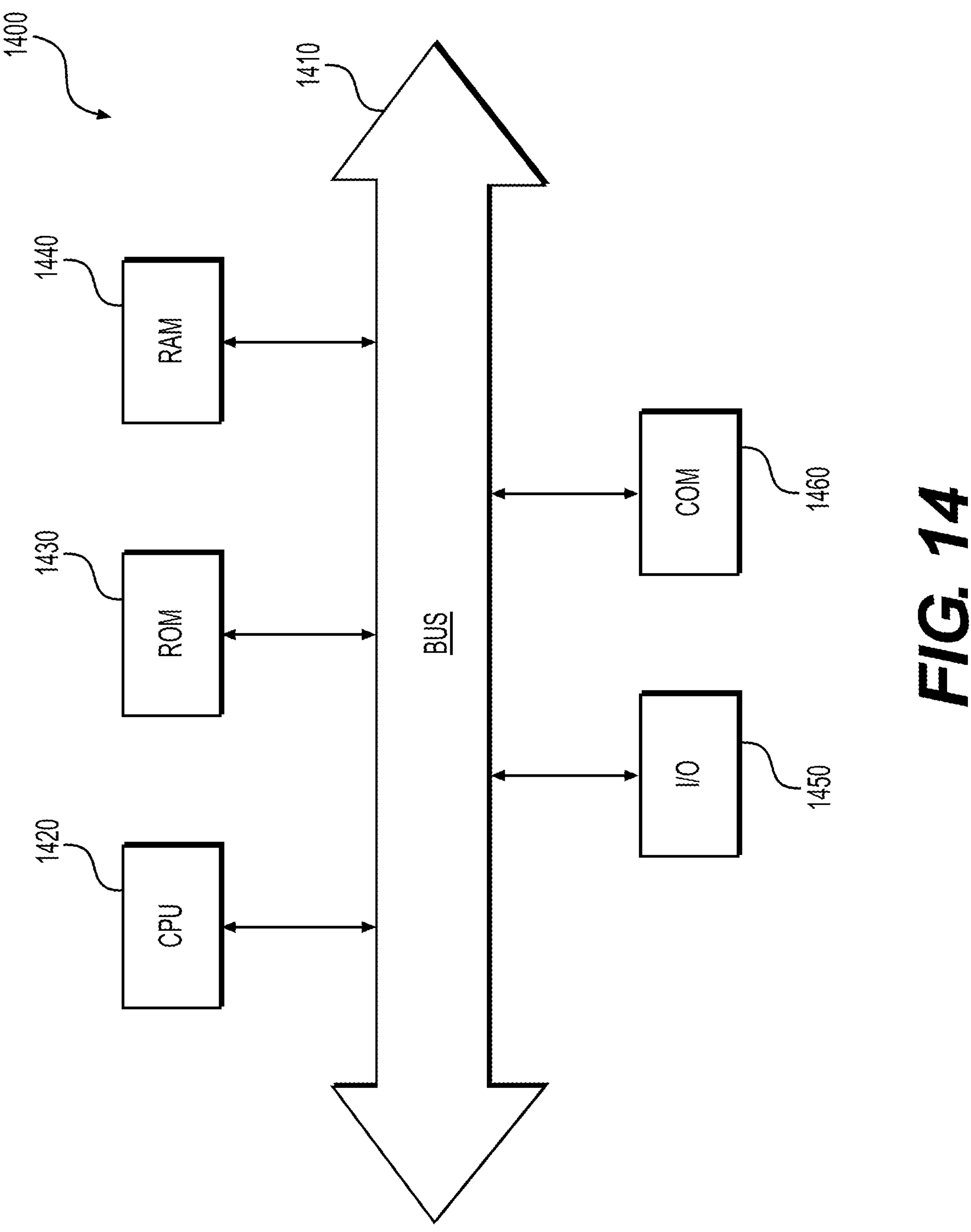
FIG. 14 depicts an example of a computing device that may execute techniques presented herein, according to one or more embodiments.

As shown in FIG. 14, device 1400 may include a central processing unit (CPU) 1420. CPU 1420 may be any type of processor device including, for example, any type of special purpose or a general-purpose microprocessor device. As will be appreciated by persons skilled in the relevant art, CPU 1420 also may be a single processor in a multi-core/multiprocessor system, such system operating alone, or in a cluster of computing devices operating in a cluster or server farm. CPU 1420 may be connected to a data communication infrastructure 1410, for example a bus, message queue, network, or multi-core message-passing scheme.

Device 1400 may also include a main memory 1440, for example, random access memory (RAM), and also may include a secondary memory 1430. Secondary memory 1430, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 1430 may include similar means for allowing computer programs or other instructions to be loaded into device 1400. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 1400.

Device 1400 also may include a communications interface ("COM") 1460. Communications interface 1460 allows software and data to be transferred between device 1400 and external devices. Communications interface 1460 may include a modem, a network interface (such as an Ethernet card), a communications port, a PCMCIA slot and card, or the like. Software and data transferred via communications interface 1460 may be in the form of signals, which may be electronic, electromagnetic, optical or other signals capable of being received by communications interface 1460. These signals may be provided to communications interface 1460 via a communications path of device 1400, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 1400 may also include input and output ports 1450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Systems and methods disclosed herein may use AI to interpolate and integrate information in different formats (text, image, genetic, etc.) from disparate sources of a pathology report and display them to a user (e.g., pathologist) allowing for histo-spatial correlation, and potentially radiologic-genomic correlation.

The use of AI to extract text information from an anatomic pathology laboratory information system (AP LIS) and displaying the extracted text information may be applied to multiple contexts. For example, rather than extracting context specific information from one organ in one pathology case, AI may also be used to extract diagnostic information from multiple cases from one patient, and the extracted information from these multiple cases may be displayed on a diagnostic timeline. AI may also be used to extract diagnostic information from multiple cases from one patient, and this extracted information may be displayed on a mock organ map.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:

1. A computer-implemented method for processing electronic medical images, comprising:

receiving, via a slide analysis tool, a plurality of medical images of at least one pathology specimen, the at least one pathology specimen being associated with a patient;

receiving, via the slide analysis tool, a gross description, the gross description including data associated with at least one aspect of the plurality of medical images, the data including information about a size, a shape, or an appearance of the at least one pathology specimen based on an examination of the plurality of medical images;

determining, via the slide analysis tool, the data from the gross description by:

extracting at least a first portion of the data from the gross description, and inferring at least a second portion of the data of the gross description from the plurality of medical images via a gross description inference module of the slide analysis tool;

determining, using a machine learning system of the slide analysis tool, at least one associated location on the plurality of medical images for the determined data from the gross description; and outputting in relation to the plurality of medical images, via a display, a visual indication of one or both of (i) the determined data from the gross description or (ii) the at least one associated location on the plurality of medical images.

2. The method of claim 1, further comprising:

determining if the gross description is structured or unstructured;

upon determining that the gross description is structured, providing the gross description to a rule-based AI system; and upon determining the gross description is unstructured, providing the gross description to a natural language processing based machine learning system.

3. The method of claim 1, further comprising:

receiving a corresponding radiologic image associated with the patient; and determining a sample location of the plurality of medical images relative to the corresponding radiologic image.

4. The method of claim 3, further comprising:

displaying the sample location of the plurality of medical images relative to the corresponding radiologic image.

5. The method of claim 1, further comprising:

receiving a corresponding three-dimensional figure associated with the patient; and determining a sample location of the plurality of medical images relative to the corresponding three-dimensional figure.

6. The method of claim 1, further comprising:

comparing the at least one associated location of the data on the plurality of medical images with an external system, wherein any discrepancies are marked.

7. The method of claim 1, further comprising:

determining that diseased tissue is present in two or more of the plurality of medical images; and determining a location of the diseased tissue in three-dimensions based on the determined presence of the diseased tissue within the plurality of medical images.

8. The method of claim 7, further comprising:

estimating an area and/or volume of the diseased tissue.

9. The method of claim 1, further comprising:

determining a new coordinate system for measurement data of lesions within the plurality of medical images.

10. The method of claim 1, further comprising:

inferring genomic characteristics about a tumor based on data describing one or more alternative tumors within the patient.

11. A system for processing electronic medical images, the system comprising:

at least one memory storing instructions; and at least one processor configured to execute the instructions to perform operations comprising:

receiving, via a slide analysis tool, a plurality of medical images of at least one pathology specimen, the at least one pathology specimen being associated with a patient;

receiving, via the slide analysis tool, a gross description, the gross description including data associated with at least one aspect of the plurality of medical images, the data including information about a size, a shape, or an appearance of the at least one pathology specimen based on an examination of the plurality of medical images;

determining, via the slide analysis tool, the data from the gross description by:

extracting at least a first portion of the data from the gross description, and inferring at least a second portion of the data of the gross description from the plurality of medical images via a gross description inference module of the slide analysis tool;

determining, using a machine learning system of the slide analysis tool, at least one associated location on the plurality of medical images for the determined data from the gross description; and outputting in relation to the plurality of medical images, via a display, a visual indication of one or both of (i) the determined data from the gross description or (ii) the at least one associated location on the plurality of medical images.

12. The system of claim 11, further comprising:

determining if the gross description is structured or unstructured;

upon determining that the gross description is structured, providing the gross description to a rule-based AI system; and upon determining the gross description is unstructured, providing the gross description to a natural language processing based machine learning system.

13. The system of claim 11, further comprising:

receiving a corresponding radiologic image associated with the patient; and determining a sample location of the plurality of medical images relative to the corresponding radiologic image.

14. The system of claim 13, further comprising:

displaying the sample location of the plurality of medical images relative to the corresponding radiologic image.

15. The system of claim 11, further comprising:

receiving a corresponding three-dimensional figure associated with the patient; and determining a sample location of the plurality of medical images relative to the corresponding three-dimensional figure.

16. The system of claim 11, further comprising:

comparing the at least one associated location of the data on the plurality of medical images with an external system, wherein any discrepancies are marked.

17. The system of claim 11, further comprising:

determining that diseased tissue is present in two or more of the plurality of medical images; and determining a location of the diseased tissue in three-dimensions based on the determined presence of the diseased tissue within the plurality of medical images.

18. The system of claim 17, further comprising:

estimating an area and/or volume of the diseased tissue.

19. The system of claim 17, further comprising:

determining a new coordinate system for measurement data of lesions within the plurality of medical images.

20. A non-transitory computer-readable medium storing instructions that, when executed by a processor, perform operations processing electronic medical images, the operations comprising:

receiving, via a slide analysis tool, a plurality of medical images of at least one pathology specimen, the at least one pathology specimen being associated with a patient;

receiving, via the slide analysis tool, a gross description, the gross description including data associated with at least one aspect of the plurality of medical images, the data including information about a size, a shape, or an appearance of the at least one pathology specimen based on an examination of the plurality of medical images;

determining, via the slide analysis tool, the data from the gross description by:

extracting at least a first portion of the data from the gross description, and inferring at least a second portion of the data of the gross description from the plurality of medical images via a gross description inference module of the slide analysis tool;

determining, using a machine learning system of the slide analysis tool, at least one associated location on the plurality of medical images for the determined data from the gross description; and outputting in relation to the plurality of medical images, via a display, a visual indication of one or both of (i) the determined data from the gross description or (ii) the at least one associated location on the plurality of medical images.

* * * * *